(12) United States Patent
Hechinger

(10) Patent No.: US 6,951,716 B2
(45) Date of Patent: *Oct. 4, 2005

(54) ANTI-PLATELET IMMUNOGLOBULIN BEAD POSITIVE CONTROL

(76) Inventor: Mark Hechinger, 700 S. Mentor Ave., Pasadena, CA (US) 91106

( * ) Notice: Subject to any disclaimer, the term of this patent is extended or adjusted under 35 U.S.C. 154(b) by 245 days.

This patent is subject to a terminal disclaimer.

(21) Appl. No.: 10/163,966

(22) Filed: Jun. 6, 2002

(65) Prior Publication Data

US 2003/0032068 A1 Feb. 13, 2003

Related U.S. Application Data

(63) Continuation of application No. 09/678,706, filed on Oct. 3, 2000, now abandoned, which is a continuation-in-part of application No. 08/869,727, filed on Jun. 5, 1997, now abandoned, which is a continuation-in-part of application No. 08/404,144, filed on Mar. 13, 1995, now abandoned.
(60) Provisional application No. 60/015,873, filed on Jun. 5, 1996.

(51) Int. Cl.$^7$ .................. G01N 33/53; G01N 33/543
(52) U.S. Cl. ..................... 435/4; 435/6; 435/7.1; 435/7.2; 435/7.92; 435/7.93; 435/7.94; 435/7.95; 435/967; 435/973; 436/10; 436/63; 436/501; 436/506; 436/507; 436/509; 436/513; 436/518; 436/519; 436/523; 436/524; 436/527; 436/528; 436/531; 436/533; 436/534; 436/536; 436/538; 436/546; 436/805; 436/811
(58) Field of Search ................. 435/4, 6, 7.1, 967, 435/973, 7.92–7.95; 436/10, 507, 513, 518, 523, 524, 527, 533, 501, 534, 506, 509, 528, 531, 546, 805, 811

(56) References Cited

U.S. PATENT DOCUMENTS

| | | | | |
|---|---|---|---|---|
| 5,286,452 A | * | 2/1994 | Hansen | 422/73 |
| 6,268,222 B1 | * | 7/2001 | Chandler et al. | 436/523 |
| 6,280,618 B2 | * | 8/2001 | Watkins et al. | 210/222 |
| 2003/0008410 A1 | * | 1/2003 | Hechinger | 436/172 |
| 2003/0194818 A1 | * | 10/2003 | Hechinger | 436/513 |

OTHER PUBLICATIONS

Greenwalt et al. An enzyme linked antiglobulin test to quantify nanogram quantities of IgG on polystyrene microspheres. Vox Sang. 63 (4) pp. 272–275 (1992).*

Saunders et al. Amplified flow–cytometric separation–free fluorescence immunoassays. Clin. Chem. 31 (12) pp. 2020–2023 (1985).*

Fluwyler et al. Flow Microsphere Immunoassay for the Quantitative and Simultaneous Detection of Multiple Soulble Analytes. Methods in Cell Biology. vol. 33. pp. 613–629 (1990).*

* cited by examiner

Primary Examiner—Chris Chin
Assistant Examiner—Kartic Padmanabhan
(74) Attorney, Agent, or Firm—Colin P. Abrahams

(57) ABSTRACT

Immunoassay methods and apparatus are provided which utilize flow cytometry, coated latex microspheres, and fluorochrome labeled antibodies, to simultaneously detect the presence and amount of one or more analytes in a sample. Beads of several different sizes, colors or shapes, each bead are coated with a different analyte, for the simultaneous detection of one or more analytes and of cell components. The invention is also directed to platelet Ig positive control reagents and assays which provide for the setting of the fluorescence positive region for each patient. The platelet control is sized to fit between the platelets and red cells and thus making it ideal as a true biological control.

12 Claims, 36 Drawing Sheets

BEAD DETECTION SYSTEM

ATTACHED INDICATOR SYSTEM

ANTI-SPECIES ANTIBODY

PRIMARY ANTIBODY AGAINAT AG.

BOUND ANTIGEN

LATEX BEAD CARRIER

Fig. 5 Microspheres of different sizes (4, 5, 6, 7, and 10 μm) as seen with flow cytometer forward and side (90°) light scatter.

Fig. 6 Antigen labeled microspheres incubated with negative serum.

Fig. 7  Antigen labeled microspheres incubated with a serum containing antibody to Scl-70 but negative for antibodies to the four other antigens.

Fig 8  Schematic presentation illustrating combination of different bead sizes with two different flucrochromes for two color flow cytometry. Differences in bead sizes not shown, but would be seen in three dimensional plot.

Fig. 9 - Clinical Bead Trials - Sensitivity Graph with Mean Channel Fluorescence in EU/mL Positive Serum Dilutions Antigens

|        | 1:1   | 1:2   | 1:4   | 1:8   | 1:16  | 1:32  | 1:64  | 1:128 |
|--------|-------|-------|-------|-------|-------|-------|-------|-------|
| RNP    | 82.6  | 100.2 | 118.9 | 136.3 | 131.5 | 164.8 | 208.3 | 186.9 |
|        | 95.0  | 47.5  | 23.8  | 11.9  | 5.9   | 2.9   | 1.5   | 0.8   |
| SM     | 86.0  | 100.6 | 125.5 | 137.6 | 158.4 | 197.5 | 197.3 | 177.9 |
|        | 100.0 | 50.0  | 25.0  | 12.5  | 6.3   | 3.2   | 1.6   | 0.8   |
| SSA    | 77.4  | 79.8  | 89.0  | 96.2  | 112.4 | 124.1 | 155.6 | 195.3 |
|        | 80.0  | 40.0  | 20.0  | 10.0  | 5.0   | 2.5   | 1.3   | 0.7   |
| SSB    | 54.8  | 64.4  | 70.4  | 76.7  | 86.5  | 105.3 | 120.5 | 155.0 |
|        | 80.0  | 40.0  | 20.0  | 10.0  | 5.0   | 2.5   | 1.3   | 0.7   |
| SCL-70 | 72.6  | 90.5  | 97.8  | 107.4 | 111.0 | 127.8 | 164.9 | 151.9 |
|        | 110.0 | 55.0  | 27.5  | 13.8  | 6.9   | 3.5   | 1.8   | 0.9   |
|        |       |       |       |       |       |       |       |       |
| RNP    | SM    | SSA   | SSB   | SCL-70 |      |       |       |       |

RHEUMO-BEADS – RNP COMPARISON

Sample    : CONTROL MIX   001
Cytometer: FACSCAN
FL1       : CT            FL2:              FL3 :

Sample    : CONTROL MIX   001
Cytometer: FACSCAN
FL1       : CT            FL2:              FL3 :

Contour statistics

Sample    : CONTROL MIX   001
Parameters : FL1  FSC      Gated events :   9979      Total events :  10000

| # | X & Y Lower | X & Y Upper | Events | % Gated | % Tot | X & Y Mean | X & Y Mode | Peak |
|---|---|---|---|---|---|---|---|---|
| 1 | 1.00 21 | 18.61 63 | 3396 | 34.03 | 33.96 | 3.75 33.55 | 2.08 26.00 | 160 |
| 2 | 21.54 21 | 10000 63 | 42 | 0.42 | 0.42 | 29.61 46.86 | 21.54 33.00 | 4 |
| 3 | 1.00 0 | 18.61 20 | 6540 | 65.54 | 65.40 | 1.42 15.23 | 1.00 17.00 | 2143 |
| 4 | 21.54 0 | 10000 20 | 1 | 0.01 | 0.01 | 80.31 13.00 | 80.31 13.00 | 1 |
| 5 | 69.39 0 | 10000 63 | 4 | 0.04 | 0.04 | 84.40 43.25 | 69.39 63.00 | 1 |
| 6 | 21.54 0 | 10000 63 | 43 | 0.43 | 0.43 | 30.79 46.07 | 21.54 33.00 | 4 |

Sample    : MIX BEADS   002
Cytometer: FACSCAN
FL1       : NORMAL CT          FL2:                    FL3 :

Contour statistics

Sample    : MIX BEADS   002
Parameters : FL1  FSC       Gated events :   9844       Total events :   10000

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9844 | 100.00 | 98.44 | 4.76 21.33 | 1.00 17.00 | 1827 |
| 2 | 69.39 0 | 10000 63 | 32 | 0.33 | 0.32 | 209.96 49.72 | 69.39 63.00 | 3 |

Sample   : MIX BEADS   003
Cytometer: FACSCAN
FL1      : RNP              FL2:              FL3 :

Contour statistics

Sample     : MIX BEADS   003
Parameters : FL1 FSC        Gated events = 9979       Total events : 10000

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9979 | 100.00 | 99.79 | 29.07 21.65 | 28.86 13.00 | 408 |
| 2 | 69.39 0 | 10000 63 | 751 | 7.53 | 7.51 | 109.98 38.85 | 69.39 25.00 | 34 |

| Sample | : MIX BEADS | 004 |
|---|---|---|
| Cytometer: FACSCAN | | |
| FL1 | : SM | FL2: FL3 : |

Contour statistics

Sample : MIX BEADS 004
Parameters : FL1 FSC   Gated events : 9973   Total events : 10000

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9973 | 100.00 | 99.73 | 33.86 21.56 | 33.40 17.00 | 711 |
| 2 | 69.39 0 | 10000 63 | 519 | 5.20 | 5.19 | 105.50 47.46 | 69.39 55.00 | 21 |

Sample : MIX BEADS 006
Cytometer: FACSCAN
FL1 : SSB          FL2:          FL3 :

Sample : MIX BEADS 006
Cytometer: FACSCAN
FL1 : SSB          FL2:          FL3 :

Contour statistics

Sample : MIX BEADS 006
Parameters : FL1 FSC   Gated events : 9981   Total events : 10000

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9981 | 100.00 | 99.81 | 14.14 21.26 | 1.00 17.00 | 1856 |
| 2 | 69.39 0 | 10000 63 | 140 | 1.40 | 1.40 | 123.05 46.94 | 92.95 57.00 | 5 |

Population Distribution

Negative Control

Comment: PLT BEAD IgM

ANTI-PLATELET IMMUNOGLOBULIN BEAD POSITIVE CONTROL

CROSS-REFERENCE TO RELATED APPLICATIONS

This application is a continuation of U.S. patent application Ser. No. 09/678,706 filed Oct. 3, 2000, abandoned which is a continuation-in-part of U.S. patent application Ser. No. 08/869,727 filed Jun. 5, 1997, abandoned which is a continuation-in-part of U.S. patent application Ser. No. 08/404,144, filed Mar. 13, 1995, abandoned and which also claims the benefit of U.S. provisional application Ser. No. 60/015,873, filed Jun. 5, 1996. All of the above applications are hereby incorporated by reference in their entirety.

FIELD AND BACKGROUND OF THE INVENTION

The present invention is directed to immunoassay methods and apparatus, and more particularly concerns an immunobead-flow cytometry method, apparatus, assay, device, system, kit, and the like for detecting and quantifying platelets, antigens, antibodies and the like.

Microsphere based assays using flow cytometry have been reported by several investigators after Horan et al. reported the use of polystyrene microspheres to detect serum rheumatoid factor in 1979).

The merger of bead assays with flow cytometry has been demonstrated in several clinical applications, e.g. detection of antibodies to CMV and herpes simplex; detection of antibodies to different components of the human immunodeficiency virus (HIV); detection of antibodies to several antigens of *Candida albicans*; detection of human anti-mouse antibody (HAMA) in transplant patients receiving OKT3; detection of circulating immune complexes and HIV antibody in immune complexes; and detection of two different antibodies to CEA.

Although interest has focused on the detection of antibodies and antigens in fluids, the use of other ligand systems and biological probes has been explored, e.g. competitive binding of antibiotics to DNA coated beads and detection of viruses.

Although the principals and advantages of fluorescent microsphere immunoassays have been discussed in the literature, applications in clinical lab testing have been relatively few despite the economics of time and cost inherent in this technology.

Within the realm of flow cytometric applications and ever increasing interest in bead based technologies, it has been difficult, if not impossible to conceive the applications potentially available. One of these applications involves the entire spectrum of clinical laboratory testing.

Within the field of the Invention for Anti-platelet antibody bead positive control comes a multitude of other applications for the testing of immunologic material utilized in analytical testing. Any antigen, antibody, protein, chemical or ligand and be tested for its presence or viability by application to a bead based substrate and tested using immunological principles. For example, in the current Field of Invention we are testing for human immunoglobulins on the surface of patient platelets in disease states associated with immune or non-immune thrombocytopenia. Unfortunately, the secondary markers added to patient platelets can not be optimally tested for it's reactivity because of the lack of human platelets coated with a specific patient immunoglobulin for IgG, A, or M (e.g. a positive control). Therefore, the anti-Platelet positive control beads were designed to fill this void and to obtain a higher level of confidence that the anti-platelet antibody assay performed in the laboratory was utilizing reagents viable enough to justify the end result. To do this, latex beads were coated with human immunoglobulins, IgG, IgA, and IgM, thus mimicking the positive platelet itself. Within this system, bead size is dependent of the system you are testing them in. For platelet assays, the size of the coated bead must fall within 4 to 10 microns for easy detection without red cell, white cell or platelet size interference.

Applying this system to other assays with hard to find positive controls and/or antibody/antigen systems, any positive selection product can be made. Within this embodiment we demonstrate examples of positive control bead material for use with chemistry analytes, tumor markers, protein derivatives, and antibody/antigen systems. A confirmatory bead based substrate material has many applications in both clinical laboratories and industrial environments; especially when complex confirmatory material is hard to acquire. Furthermore, multiple bead sizes may be utilized, simultaneously, in the same reaction (assay) system to test multiple analyte integrity.

SUMMARY OF THE INVENTION

In accordance with the present invention, there is provided an Anti-Platelet Antibody Positive Immunoglobulin (Ig) Control.

The use of microspheres, beads, or other particles as solid supports for antigen-antibody reactions in order to detect antigens or antibodies in serum and other body fluids is particularly attractive when linked to flow cytometry. Flow cytometers have the capacity to detect particle size differences and are highly sensitive to fluorescence indicators.

Microspheres can be "sized" by forward angle light scatter (FALS) or electronic volume. Used in conjunction with right angle light scatter (RALS)(eg. The internal complexity of the particle), a flow cytometer (FCM) can distinguish between single and aggregated particles (doublets). By combining FALS with fluorescent properties, it is practical to use beads of several different sizes, each bead coated with a different protein, and/or detected with a variety of different fluorochrome indicators, for the simultaneous detection of multiple analytes (antigens or antibodies). Microspheres can be coated with proteins passively or covalently depending on their chemical makeup.

The strengths of this type of assay are: 1) the ability to simultaneously, but discretely, analyze multiple analytes; 2) the simplicity of binding proteins to microspheres; 3) the ability of flow cytometry (FCM) to detect small particle size differences; 4) the exquisite sensitivity of FCM as a detector of different wavelengths of fluorescence, simultaneously; 5) the usefulness of applying other material to the bead particles; and 6) utilizing beads coated with purified material to confirm the reaction characteristics with other antibodies, antigens, ligands, chemicals, proteins, or conjugates.

Available auto-sampling systems make it even more appealing in this regard. The capacity to simultaneously detect multiple analytes in one tube in a immunoassay system suggests that immunoassays and biological probe assays may ultimately mimic multi-channel chemistry analyzers with all of their benefits.

In accordance with one embodiment of the present invention, there is provided an Anti-platelet Immunoglobulin Beads Positive Control.

In accordance with another embodiment of the invention, there is provided a Positive Control Immunobead Assays.

By attaching each of these antigens to different sized latex beads, the presence of antibodies to one or more of these antigens can be rapidly detected and semi-quantitated. Instead of the five or more separate assays currently required, one assay involving five or more beads of different sizes in one tube provides the information needed. The cost saving in terms of materials, supplies, and technician time are estimated to be 60–70%. This can be further enhanced by utilizing robotic auto-sampling devices currently available or being developed for flow cytometry, for example, the Becton Dickinson Calibin with an auto-loader.

In accordance with another aspect of the present invention, a platelet immunoglobulin (Ig) positive control reagent and assay are provided which utilize flow cytometry, coated and/or non-coated latex beads, and labeled antibodies, are used to detect and quantify one or more analytes, and types of platelets, to provide a positive control for each patient. In accordance with one embodiment of the present invention, immunoglobulin coating for IgG, IgM or IgA is bound to one or more sized latex beads, and stabilized for extended shelf life. In accordance with a direct procedure, an amount of Ig bead control material is added to respective tubes labeled Control, IgG, IgM, and IgA. Thereafter, patient and control platelets (Type O) are added to the respective tubes. After incubation, a goat IgG-FITC and goat anti-human Ig-FITC are added to the Control and IgG, IgM, and IgA tubes, respectively. The tubes are incubated, washed, resuspended and read on a flow cytometer using forward scatter versus fluorescence (FL1). Then, the positive region is set based on the negative control tube for that patient containing specie specific isotypic antisera. In accordance with an indirect procedure, type O platelets are incubated with an amount of control or patient serum in respective tubes labeled Control, IgG, IgM, and IgA. After incubation the tubes are washed, the contents decanted and gently vortexed. Next, a quantity of Ig coated bead control material is added to each tube labeled Control, IgG, IgM, and IgA. Next, goat Ig-FITC and goat anti-human Ig-FITC is added to the IgG, IgM, and IgA tubes. Species specific Ig FITC conjugate is added to the control tube. The tubes are vortexed, incubated, washed, resuspended, and read on a flow cytometer using forward scatter versus fluorescence (FL1.) The positive region is then set based on the control tube for that patient.

The principal object of the present invention is the provision of an immunobead-flow cytometry assay for simultaneously detecting a plurality of antigens or antibodies in a sample.

The focus of this invention is the design of a Anti-platelet antibody control bead is to validate the anti-human Ig F(ab')2 fluorescenated antibody used in the detection of antibodies on patients. Because of the rarity and complexity in storage of an actual positively coated platelets with each of the three main immunoglobulins used in this assay, it was necessary to develop another synthetic control system (e.g. this invention). Use within the assay also takes into consideration the size of the bead to be utilized. Because red blood cells and platelets are very close in size, the bead of choice has to be one or varied sizes which would, by scatter properties, appear in between each of these cellular components. Obviously, this invention utilizes examples of various sizes, however, depending on the test system, size may not be an issue.

Superimposing this invention into other testing systems, whether controls are available or not, bead based positive and negative controls can verify a multitude of clinical and commercial products. This can be as simple as by binding an analyte to a specific size bead and following-up with a secondary fluorescent marker specific for the captured antigen and run through a flow cytometer for fluorescent intensity readings or by pre/post quantitation of supernatants after adding an analyte to an absorption positive bead. For example, analysis for stem cells in bone marrow requires the use of an anti-CD34 antibody. Normal frequency in nature is less than 0.01% of the total cell population. Beads, coated with CD34 antigen, would help test the integrity of the anti-CD34 antibody. Therefore, the invention can be expanded to be used in reactions involving, fluorescence, absorption, negative exclusion, or any other immunologically based system. Confirmatory positive control bead assays cross all areas of science (i.e chemistry, immunology, serology, hematology, etc.) and with the availability of purified antigens, antibodies, conjugates, receptor genes, proteins, ligands, and other chemicals, the invention can be used as a verification tool for any application.

Another aspect of the present invention is the provision of a platelet Ig positive control reagent.

Still another aspect of the present invention is the provision of a platelet Ig positive control assay.

Yet another aspect of the present invention is the provision of a improved Ig coating procedure.

A multitude of aspects are added regarding the invention and it's use in the verification of analytes, proteins, antigens, antibodies, ligands, and chemicals. Capture antigens/antibodies can be added to beads of homogeneous or multi-sized diameters for use in testing reagents antigenicity, reactivity, or even non-reactivity in some circumstances. This process can occur in a pre-development or simultaneous evaluation mode; all within one reaction vessel.

Future applications are essentially unlimited because the immunoassay of the present invention can be applied to any ligand binding system and the number of simultaneous assays can be expanded by the use of combinations of fluorophores and multiple microsphere sizes.

Other aspects and further scope of the applicability of the present invention will become apparent from the detailed description to follow, taken in conjunction with the accompanying drawings wherein like parts are designated by like reference numerals.

DETAILED DESCRIPTION OF THE INVENTION

In accordance with an exemplary embodiment of the present invention, antigen coated latex surfaces, human immunoglobulus, fluorescenated antibodies against such human immunoglobulus, and flow cytometry are combined to provide multiparameter devices for the detection of a plurality of antigens in a single tube.

Often, evaluating elements that are rare events, either in a clinical medical laboratory or in manufacturing, it is difficult, if not impossible, to find material in vivo that will be stable as a positive or negative controls when performing a specific assay. The specificity of the positive bead control invention allows the investigator the ability to selectively choose purified products, which may or may not be infrequently found in natural states, but synthetically manufactured, to attach onto a variety of bead configurations. These products will be the targets (antigens) for the assay system. Thus, the invention plays a role of positive (e.g. Anti-Human Immunoglobulin Control Bead) control for rare events and assists in the quality assurance of both research, clinical, and manufacturing procedures.

Figure 1:
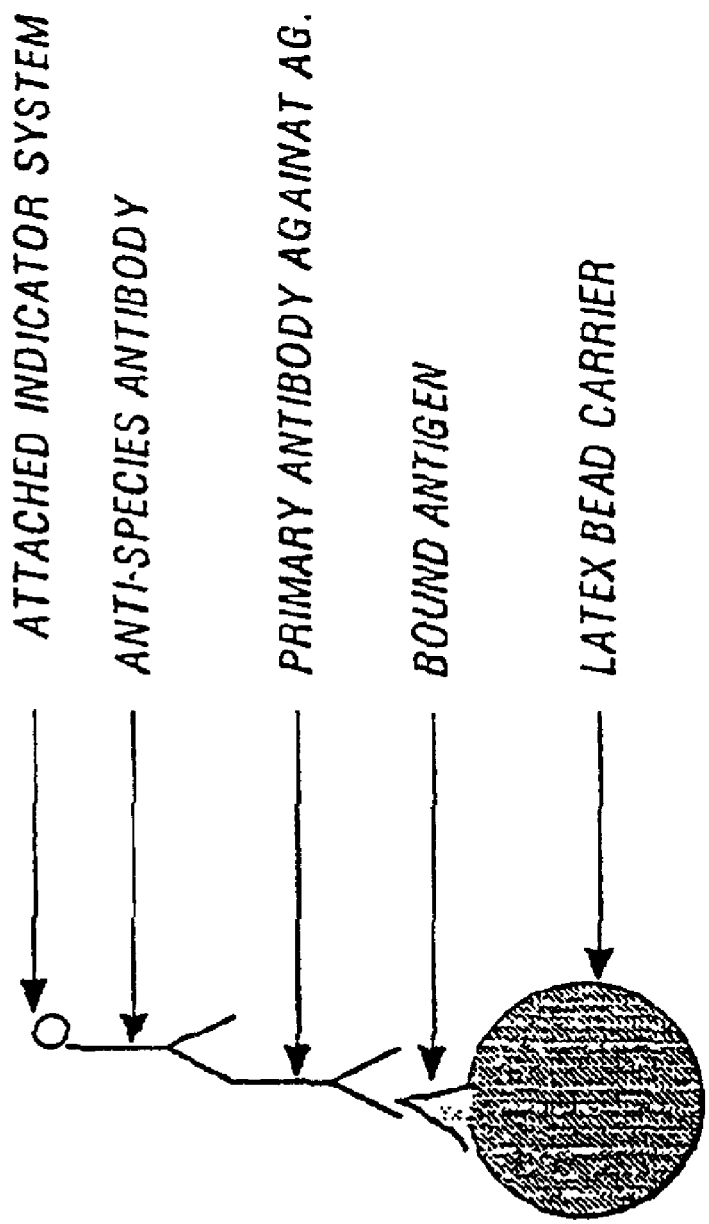
FIG. 1 is a schematic representation of an exemplary immunological structure of the bead-antigen-antibody indicator complex.

One basic principle of the present invention is to conjugate antigens or antibodies to the exterior of latex microspheres (beads) of different or same size(s). The coated microspheres are used to detect the appropriate specific antibodies or antigens simultaneously in one tube. The ability to detect multiple analytes in one reaction tube eliminates the variability often seen in results arising from separate assays. Procedurally, latex beads are coated with specific antigens or antibodies. These beads may vary in size and may also contain fluorescent dyes e.g. FITC, PE, etc. One or more of these precoated beads are then incubated with the sample (platelet, serum, body fluid) solution. If an antibody-antigen complex has been formed, a 2° indicator fluorochrome labeled antibody will bind to the appropriate bead (FIG. 1).

Figure 2:
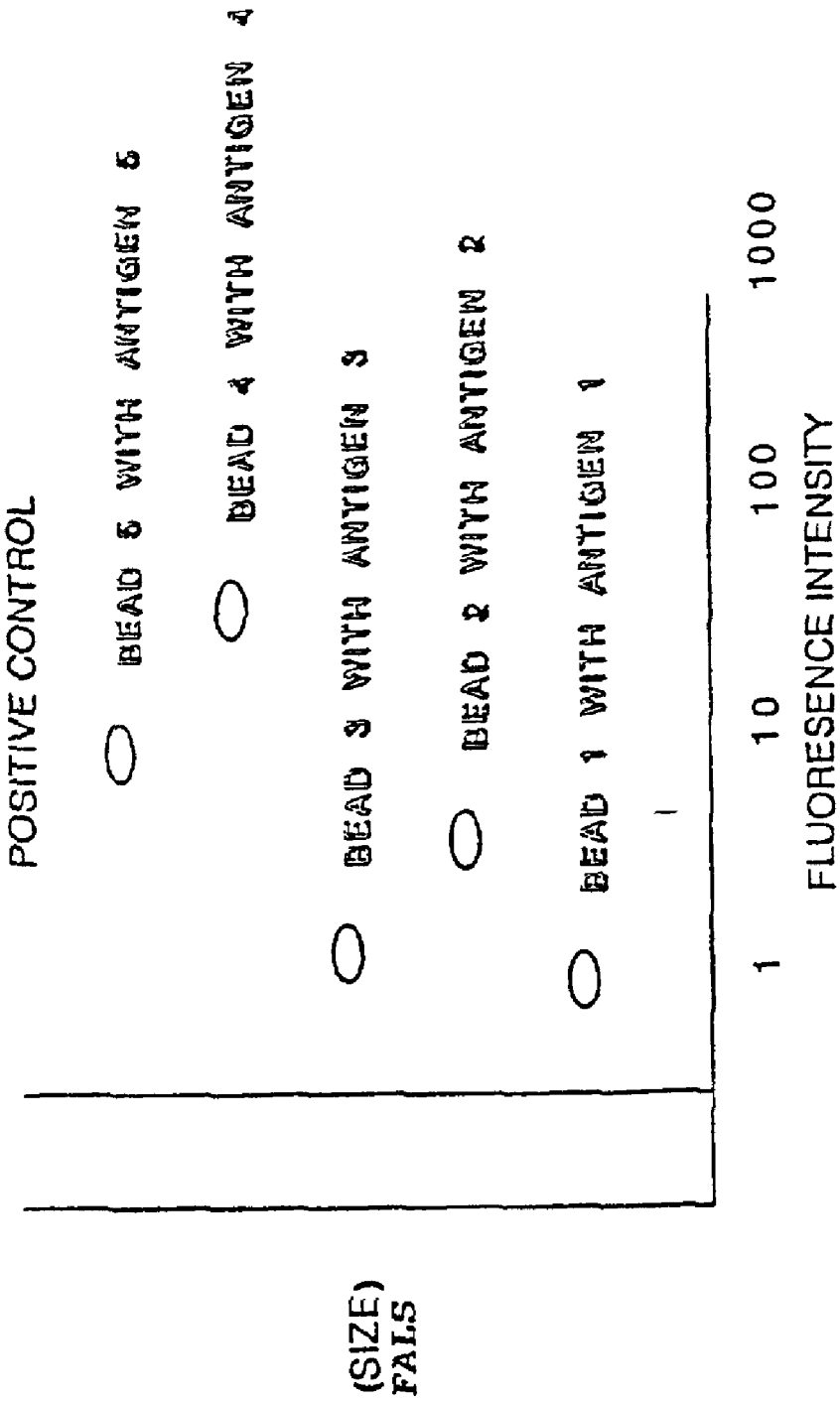
FIG. 2 is a schematic illustration of the flow cytometer histogram of forward angle light scatter (size) versus fluorescence on a positive control sample in a multiple bead system.
Figure 3:
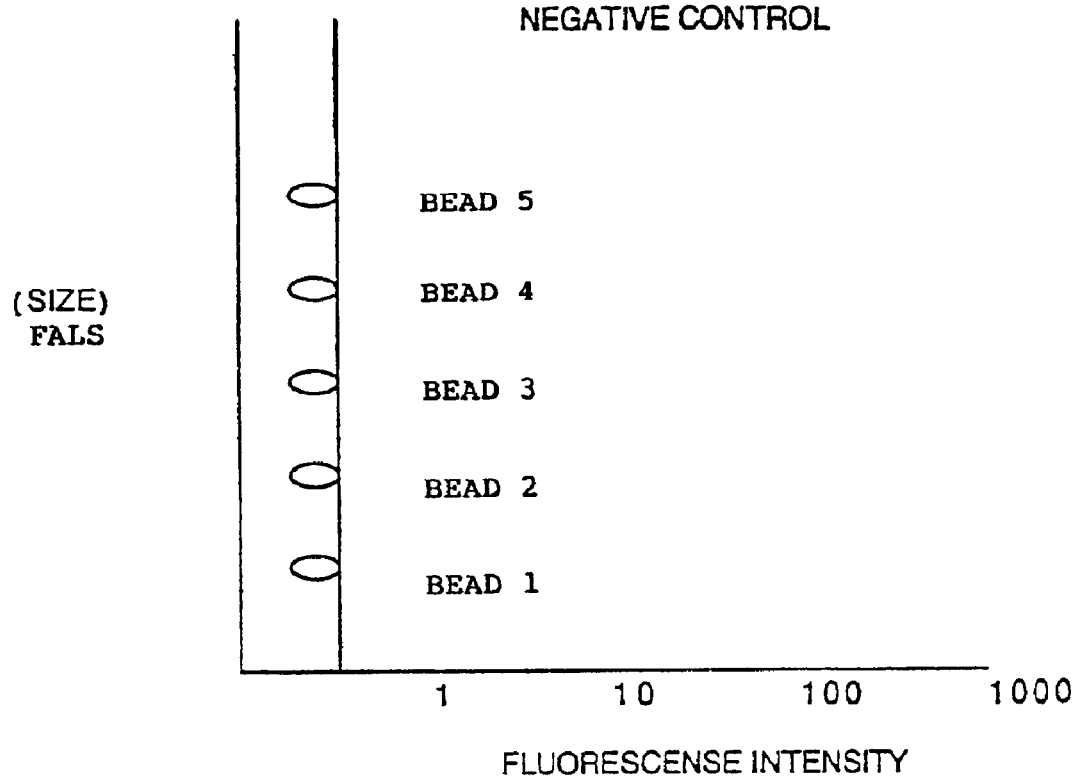
FIG. 3 is a schematic representation of a flow cytometer histogram of a negative control in a multiple bead system.

The beads are centrifuged, and may be washed, and analyzed using forward angle light scatter to discriminate the different sized beads, each bound to a different antigen or antibody, and analyzed to detect fluorescence with a flow cytometer. The solution containing beads is passed through a series of tubes until it reaches the optical quartz cell of the flow cytometer. Because of the laminar flow of sheath fluid, single particle analysis is achieved. The signal is converted from analog to a digital display representing the size of the spheres and fluorescence of each (FIG. 2). Controls are used to adjust for the fluorescence background created by electronic and particle noise (FIG. 3). A forward scatter (size) adjustment of the multiple sized bead antigen or antibody complexes is necessary in order to semi-quantitate or quantitate the relative concentration of antigen or antibody on the bead surface through single screen, visual distribution. As seen in FIG. 3, a fluorescent threshold (x-axis) is established below which fluorescence values are considered negative. Upon addition of a "positive" sample, (containing appropriate antibody or antigen), the reaction between the fluorochrome labeled indicator antibody and antigen or antibody bead complex, amplifies the fluorescence signals detected by the flow cytometer (FIG. 2). Thus, the definition of "positivity" in this system is relative to the negative control (background) and can easily be interpreted.

Figure 4:
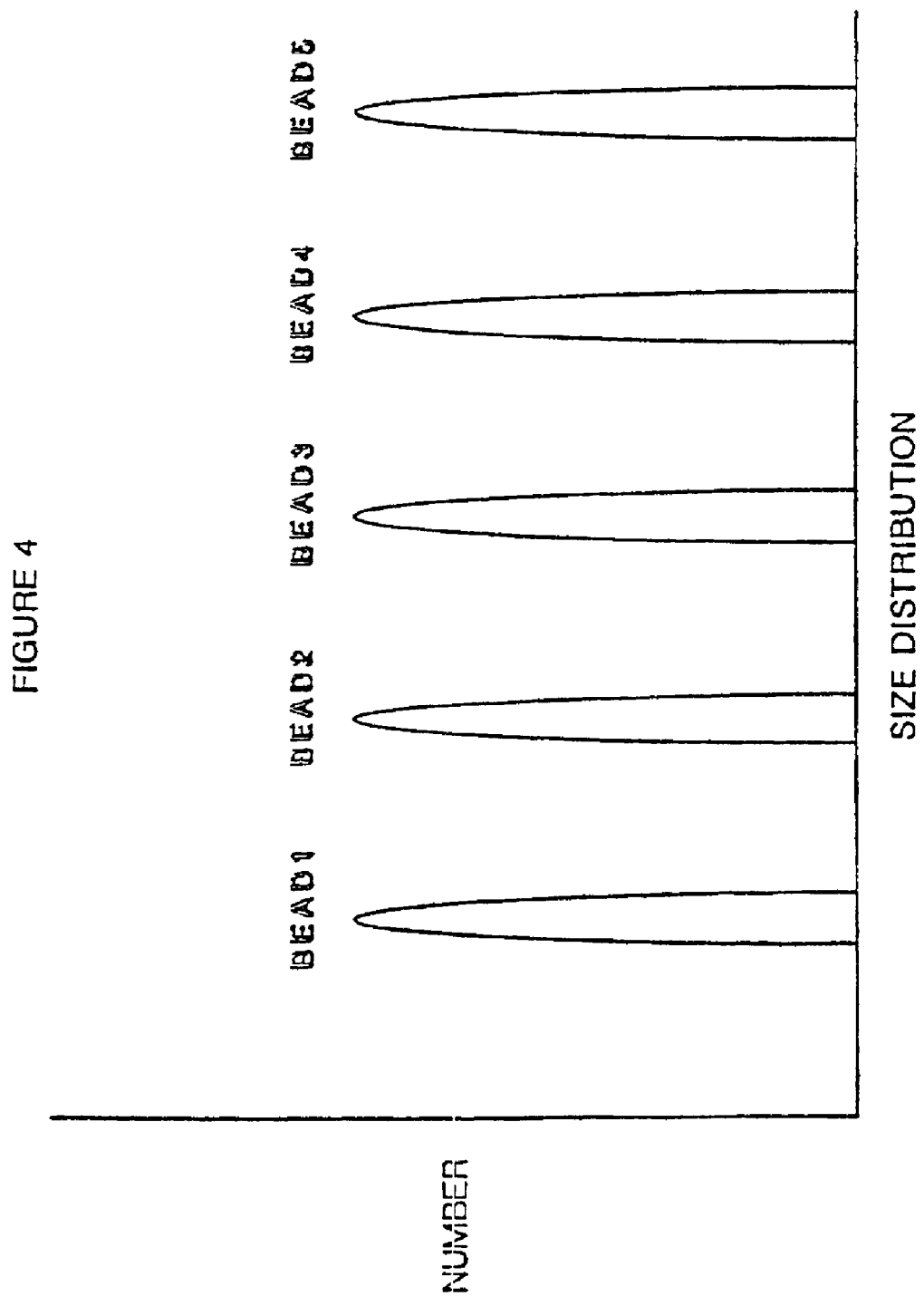
FIG. 4 is a schematic illustration of a flow cytometer histogram of the size characteristics of latex beads when run on a flow cytometer.
Figure 5:
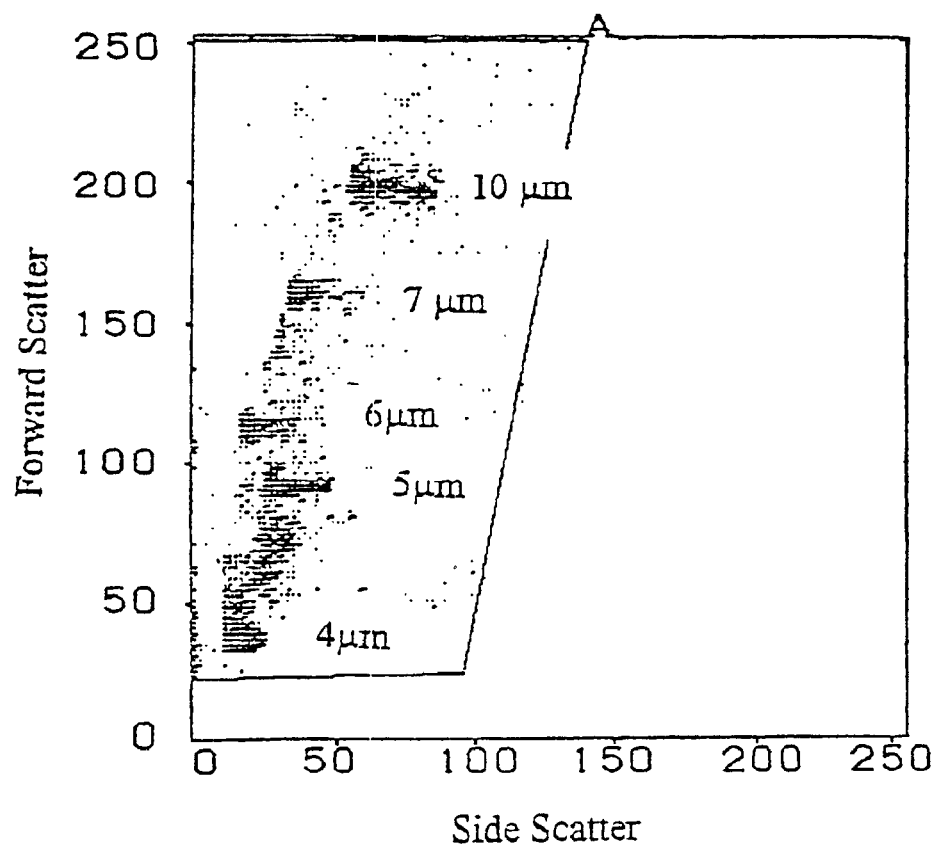
FIG. 5 is a representation of a flow cytometer cytogram of the size and complexity distribution as is seen with a patient sample of beads coated with antigen and analyzed in a flow cytometer.
Figure 6:
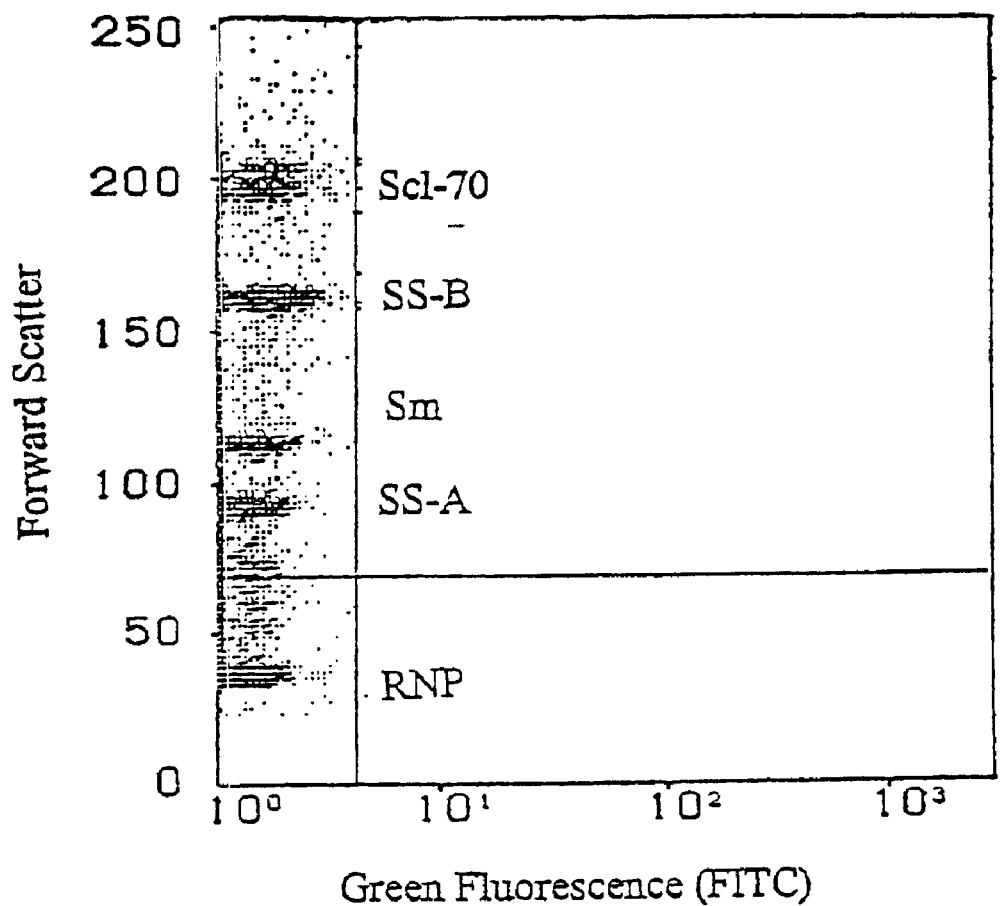
FIG. 6 is an illustration of a flow cytometer histogram of coated beads incubated with a negative control sample.
Figure 7:
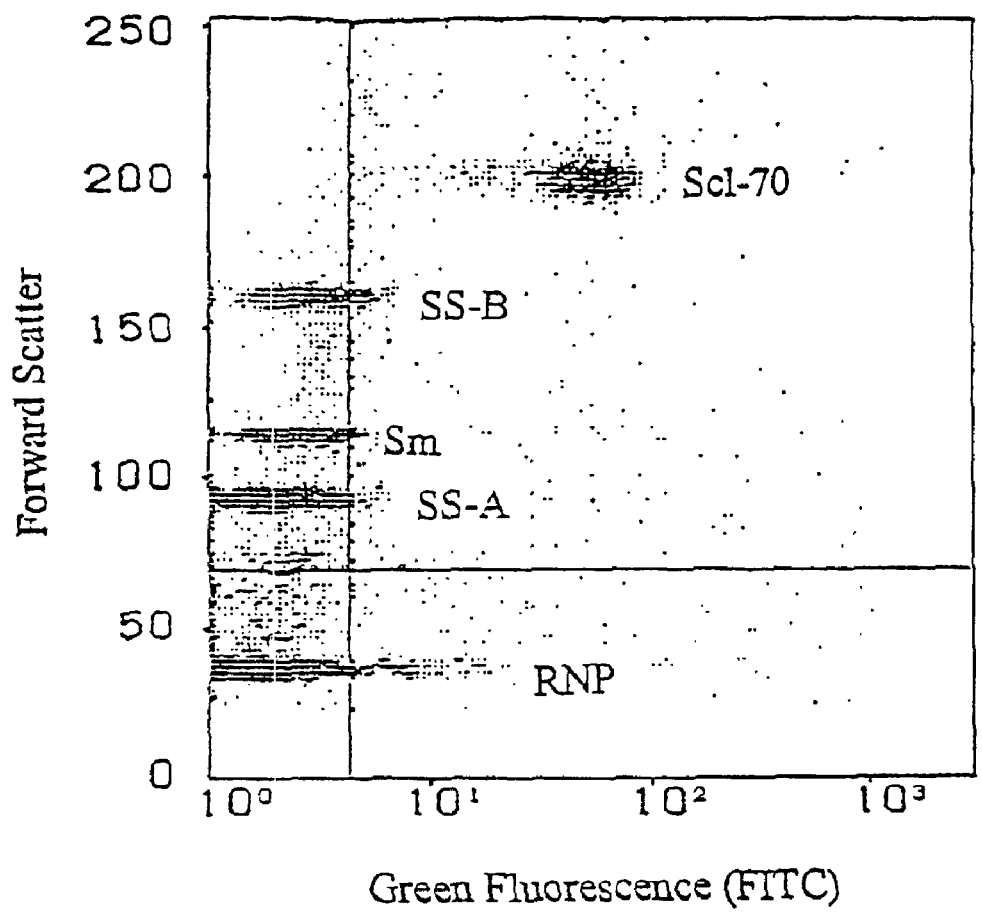
FIG. 7 is an illustration of a flow cytometer histogram of coated beads incubated with a sample containing antibody to Scl-70.

Multiple antibodies or antigens can readily be displayed and quantitative values obtained in a single two-dimensional histogram. Similarly, additional bead systems can be combined within the size distinguishing capabilities of the flow cytometer and the sizes available from vendors providing latex particles (FIG. 4). As seen in FIG. 1, the multiple antigen or antibody coated bead system incorporates specific anti-species specific 2° antibodies, labeled with fluorochromes (e.g., FITC, PE), to detect the presence of antigen-antibody complexes on the beads. Furthermore, in testing for antibody integrity, some manufacturers directly conjugated these products and thus would not require a second antibody. All other antibodies nonspecifically bound to the latex surface are either washed away or ignored by the indicator antibody.

The present invention uses the principles of flow cytometry and light scatter to detect different sizes of latex particles with fluorescence as the endpoint. Multiple antigens or antibodies in body fluids are detected simultaneously in a single tube because each specific antibody or antigen is differentiated by the size or antigen complexity of the bead it is bound to. This invention differs from the procedure disclosed in U.S. Pat. No. 5,162,863 in that the latter measures the presence of the amount of a plurality of kinds of particular antigens or antibodies in a specimen at a time by a simple construction without the use of fluorescence.

Advantages of the present invention include:
1. Because of varying sizes and dyes incorporated into microspheres, multiple antibodies or antigens can be detected and quantitated simultaneously in a single tube.
2. Specific antibodies/antigens can much more easily be detected when bound to latex bead surfaces due to the separation of one antigen/antibody from the other.
3. Because of the sensitivity of fluorescence based flow cytometry this assay tends to be capable of detecting lower levels of antibodies/antigens than other conventional assay methods e.g. EIA, ELISA, agglutination etc.
4. Because of a relatively unlimited range of bead sizes, other bead physical characteristics, fluorochromes and probes this invention offers great flexibility.
5. Single tube analysis facilitates the utilization of "batch-mode" processing and automation.
6. The present assay system can be used in screening, semi-quantitative or quantitative methods.
7. Almost any flow cytometer may be utilized for this method.
8. Minimal volumes of sample are necessary in order to run multiple assays.
9. Materials bound to the latex bead surface may be antigens, antibodies, chemicals, microorganisms, cell components, and other substances capable of binding specifically to an appropriate ligand, including DNA and RNA for in situ hybridization.

EXAMPLE 1

Platelet Quality Control Procedure—Testing Anti-Ig Integrity
1. Allow Control Beads IgG, IgA, and IgM to adjust to room temperature before use.
2. Vortex until beads are in suspension.
3. Label 5 tubes Control, IgG, IgA and IgM.
4. Add 100 uL of each of the control beads (G, A, and M) into the tube labeled control.
5. Add 100 uL of the IgG coated beads into the IgG tube, 100 uL of the IgA beads into the IgA tube, and 200 uL of the IgM beads into the IgM tube.
6. Add appropriate amount of antibody to each of the corresponding tubes.
7. Add approximately 25 uL of Type O purified platelets to each tube labeled Control, IgG, IgA and IgM.
8. Vortex gently.
9.. Incubate for 15 minutes in the dark at room temperature.
10. Add 1 ml of saline to each tube.
11. Centrifuge for 5 minutes at 800 rpm at room temperature.
12. Decant and gently vortex.
13. Add 1 ml of saline to each tube and vortex gently.
14. Analyze on Flow Cytometer. If unable to read immediately, store in the dark at room temperature.

Helpful Hints
1. Make sure beads are well mixed.
2. Antibody can be added to tubes before beads.
3. Platelets cannot be added to tubes before beads.
4. Antibody dilutions will differ depending on lot #'s.
5. The flow cytometric bead-platelet protocol will stop at 10,000 gated events.

EXAMPLE 2

Beads sizes may run from about 0.25 $\mu$m to 740.0 $\mu$m.

Other bead materials may include, polystyrene, glass, beads coated with different radical groups, methacrylate-styrene latex, traditional latex, polystyrene DVB. Possible fluorochromes include: Fluorescein isothiocyanate (FITC), Phycoerythrin (PE), Peridinin, Allochlorophyll (Per CP), Allophycocyanin, CY5, Texas Red, Propidium iodide, Ethidium bromide, and Acridine orange Antibodies which may be attached to beads or probes to detect antigens in body fluids include any monoclonal antibodies directed at infectious antigens such as, viruses, bacteria, parasites, fungi, and mycoplasma; autoantigens- (cell and cell components, such as nuclei, DNA, RNA nucleoli, membranes); cell products, such as collagen, reticulin, mucus, hormones, cytokines, neurotransmitters, coagulation factors, complement factors, mediators of inflammation (e.g. vasoconstrictive, chemotactic, enzymatic, phospholy), and enzymes; cell membrane antigens (erythrocytes-cross match, HLA-transplantation), and spermatozoa.

DNA or RNA may be attached to beads as molecular probes for the detection of infectious agents, particularly viruses (EBV, CMV, HIV, varicella-zoster, hepatitis, HPV, HCV, HBV, HTLV), oncogens and other disease related genes, in fluids by molecular hybridization.

Many of the flow cytometers now have autobiosamplers which utilize robotic arms for multiple sampling. Likewise, the entire procedure may be placed on automated pipettors/dilutors prior to the actual analysis for large scale operations.

Semi-quantitative results can now be achieved by correlating the relative fluorescence to that of a 3 or 4 decade log fluorescent histogram (0.5 or 1 log scale being the cut-off point of positivity). This is the same for any instrument used. Quantitative results may also be obtained by using pre-analyzed standards at specific EU/mL concentration on linear scale histograms.

Other examples of materials bound on beads:
a) Antigens—CA-125, PSA, ERA, PRA, etc.
b) Antibodies—anti-p24, anti-HTLV, OKT3, anti-platelet, anti-E.Coli, etc.
c) Chemicals—IL-2, Toxins, drugs, etc.
d) Microorganisms—E.coli, HTLV, viruses, etc.
e) Cell components—IL-2R, Glycoproteins, etc.
f) DNA—double stranded complement strands, etc.
g) RNA—viral RNA, etc.
h) Others—cardiolipin, pollen, metals, recombinant products, etc.

EXAMPLE 3

Multiple Dye Bead Assay
1. Determine the amount of latex bead suspension (e.g. # of drop/mL carbonate buffer) needed to achieve an event count of 900-1000 beads/second on the flow cytometer.
2. Titer antigen (Ag) to appropriate $\mu$g/mL and use concentration deemed optimal for maximum mean channel and fluorescence.
3. Add a particular antigen to each respective tube ($\mu$g)

| Size bead, fluorescent dye | Drops/mL Buffer | Ag/mL Buffer |
|---|---|---|
| 4 $\mu$m, PE | 3 | 30 |
| 5 $\mu$m, PE | 3 | 10 |
| 6 $\mu$m, PE | 6 | 15 |
| 7 $\mu$m, FITC | 6 | 15 |
| 10 $\mu$m, FITC | 10 | 10 |
| 12 $\mu$m, FITC | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume (optional).
8. Gently vortex.
9. Repeat steps 5 and 6.
10. Add 1 mL of carbonate buffer per original milliliters of antigen/bead solution.
11. Add 100 $\mu$L of each antigen/bead mixture to all reaction tubes.
12. Add 50 $\mu$L of each serum diluted to appropriately labeled tube.
13. Vortex gently and incubate for 15 minutes at room temperature.
14. Wash once with 1 mL carbonate buffer.
15. Repeat steps 5 and 6.
16. Add 20 $\mu$L of goat anti-human IgG F(ab')$^2$-FITC 1:20 (NOTE: dilution may slightly vary from lot to lot, titer all new lots).
17. Gently vortex and incubate 15 minutes at room temperature.
18. Repeat steps 5 and 6.
19. Add 0.5 mL of PBS.
20. Read on flow cytometer.

The same example may be used but with a no-wash procedure.

In accordance with an exemplary embodiment of the present invention, coated latex beads, anti-nuclear antibodies, fluorescenated antibodies against such anti-nuclear antibodies, platelets and flow cytometry are combined to provide multiparameter devices, reagents, positive controls, and for the detection and quantification of a plurality of analytes in a single tube.

Figure 26:
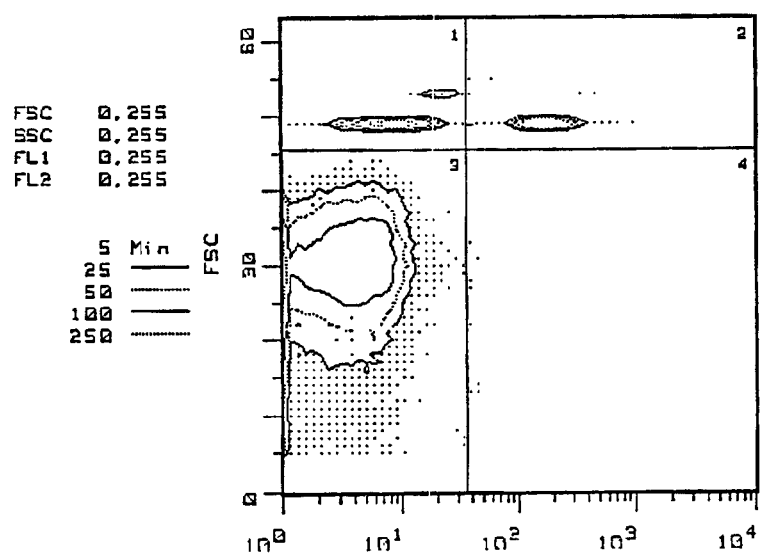
Figure 25B:
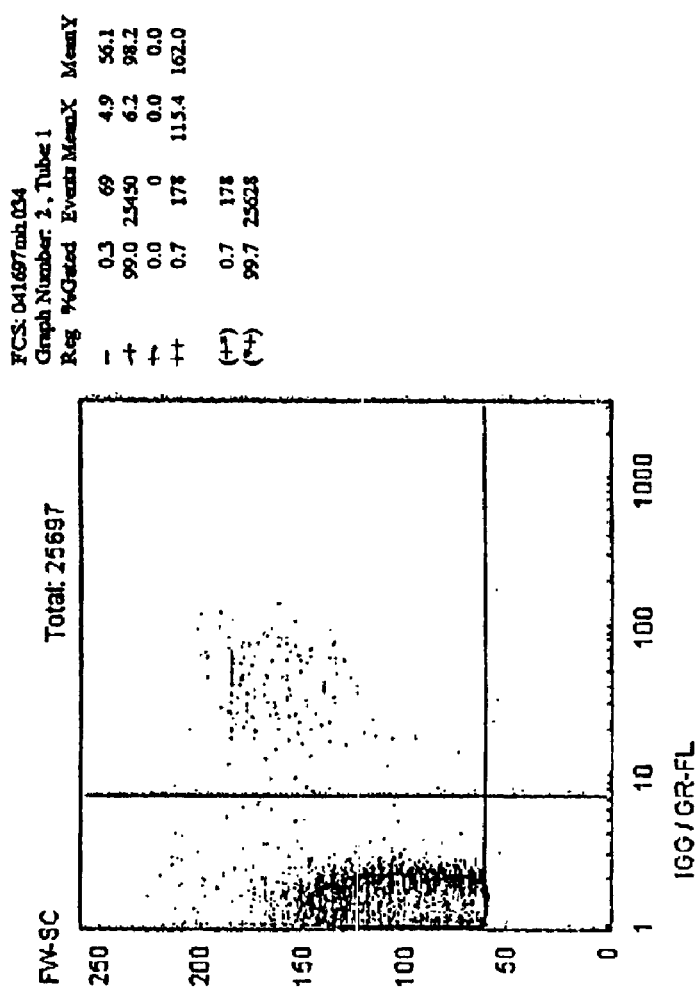
Figure 27A:
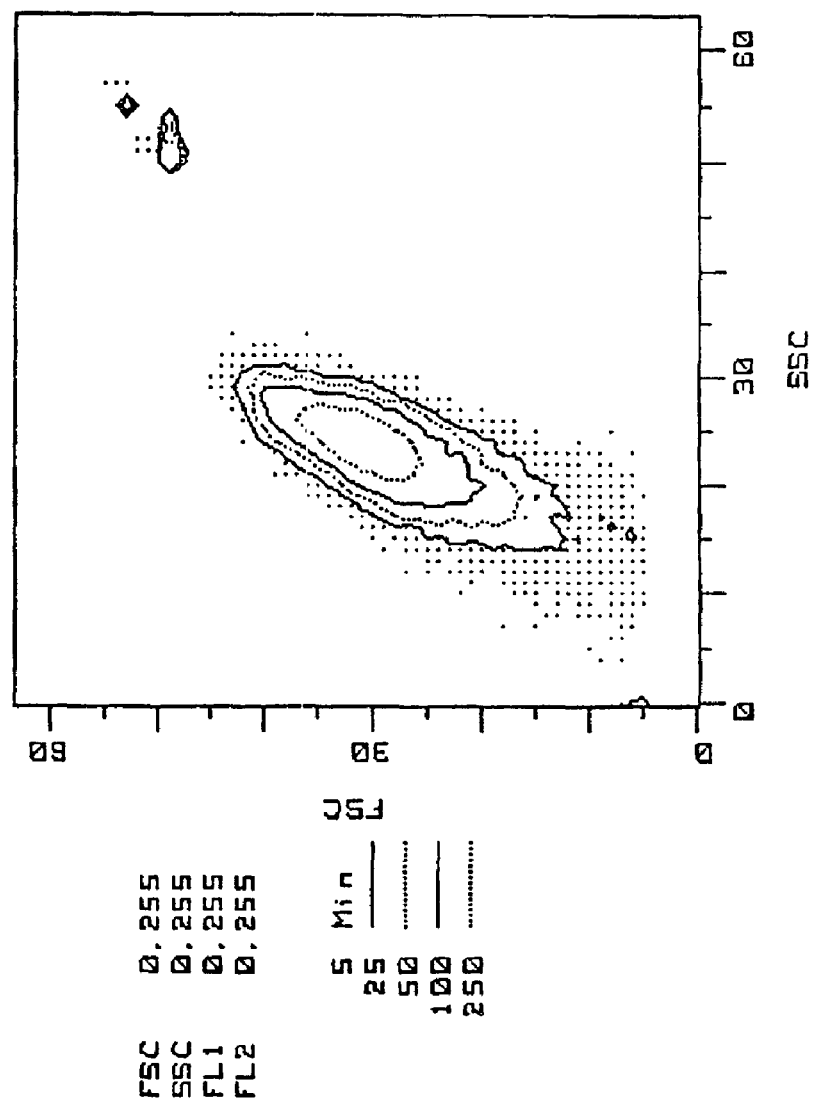
Figure 27B:
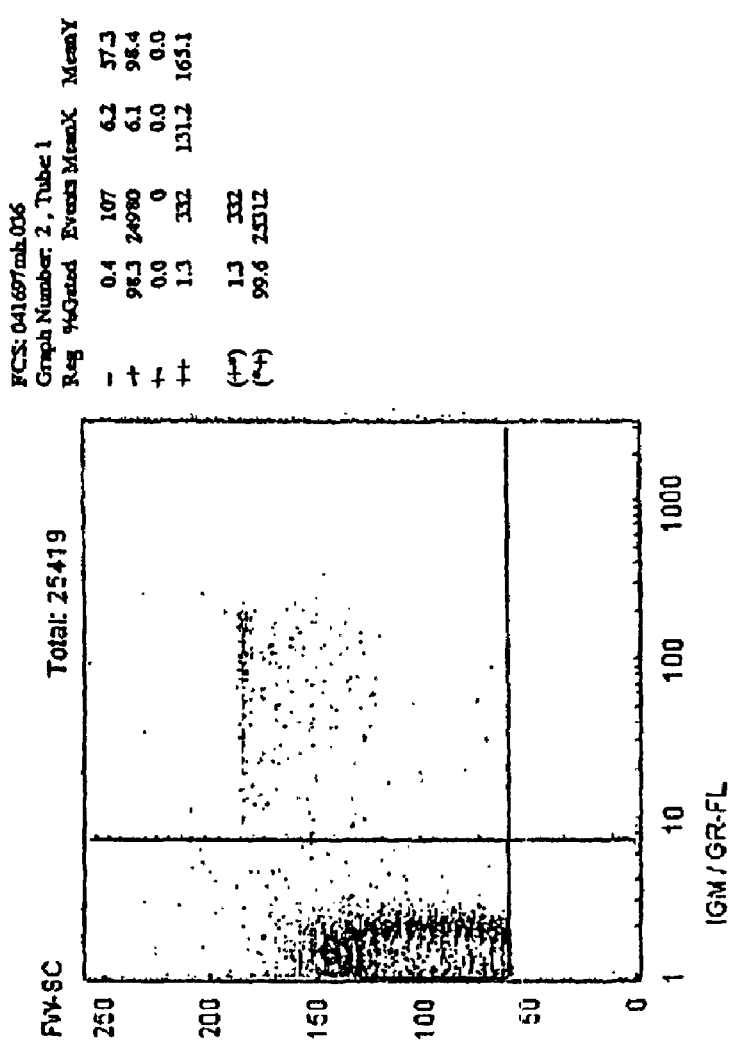
Figure 27C:
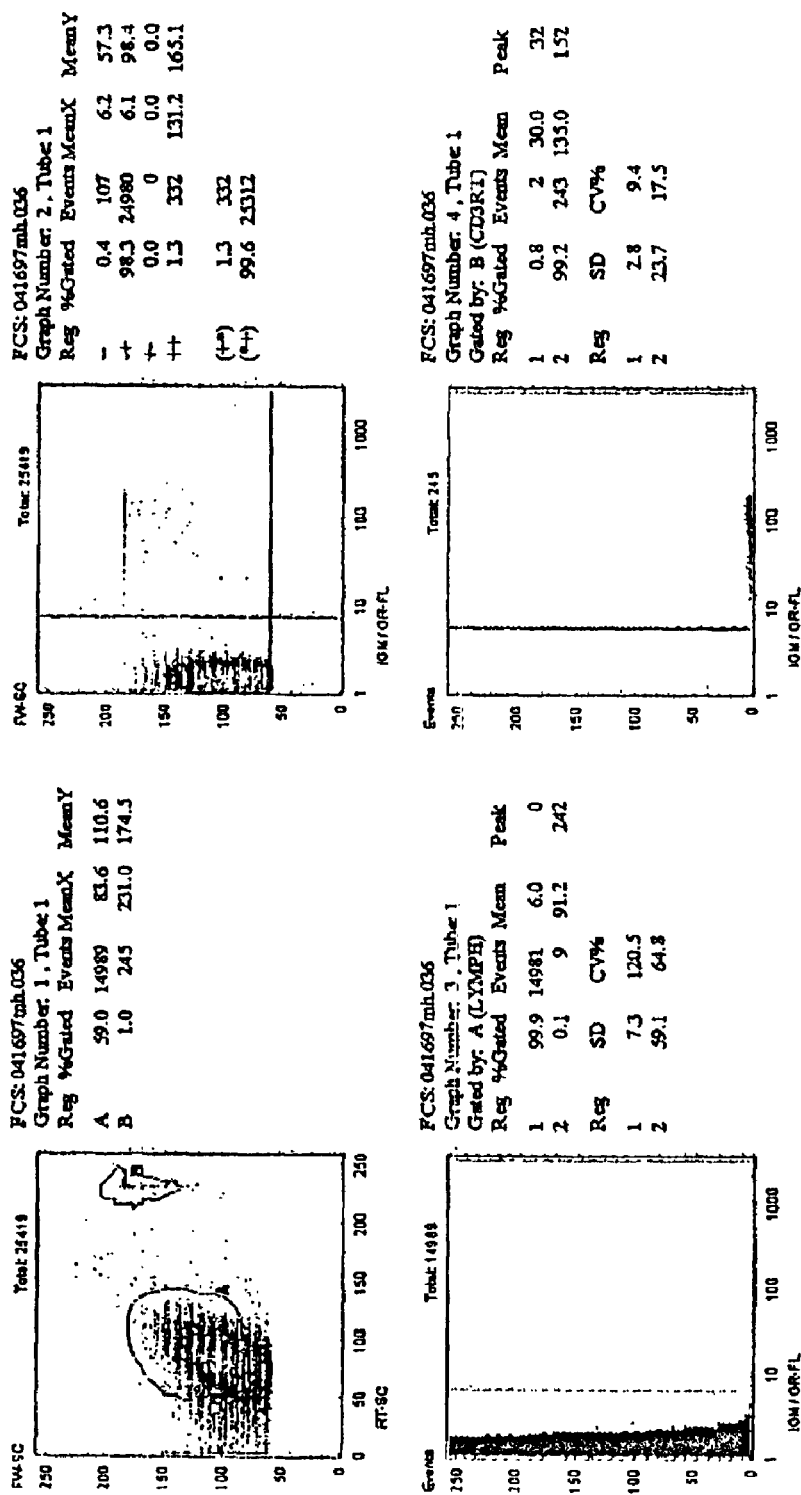
Figure 28:
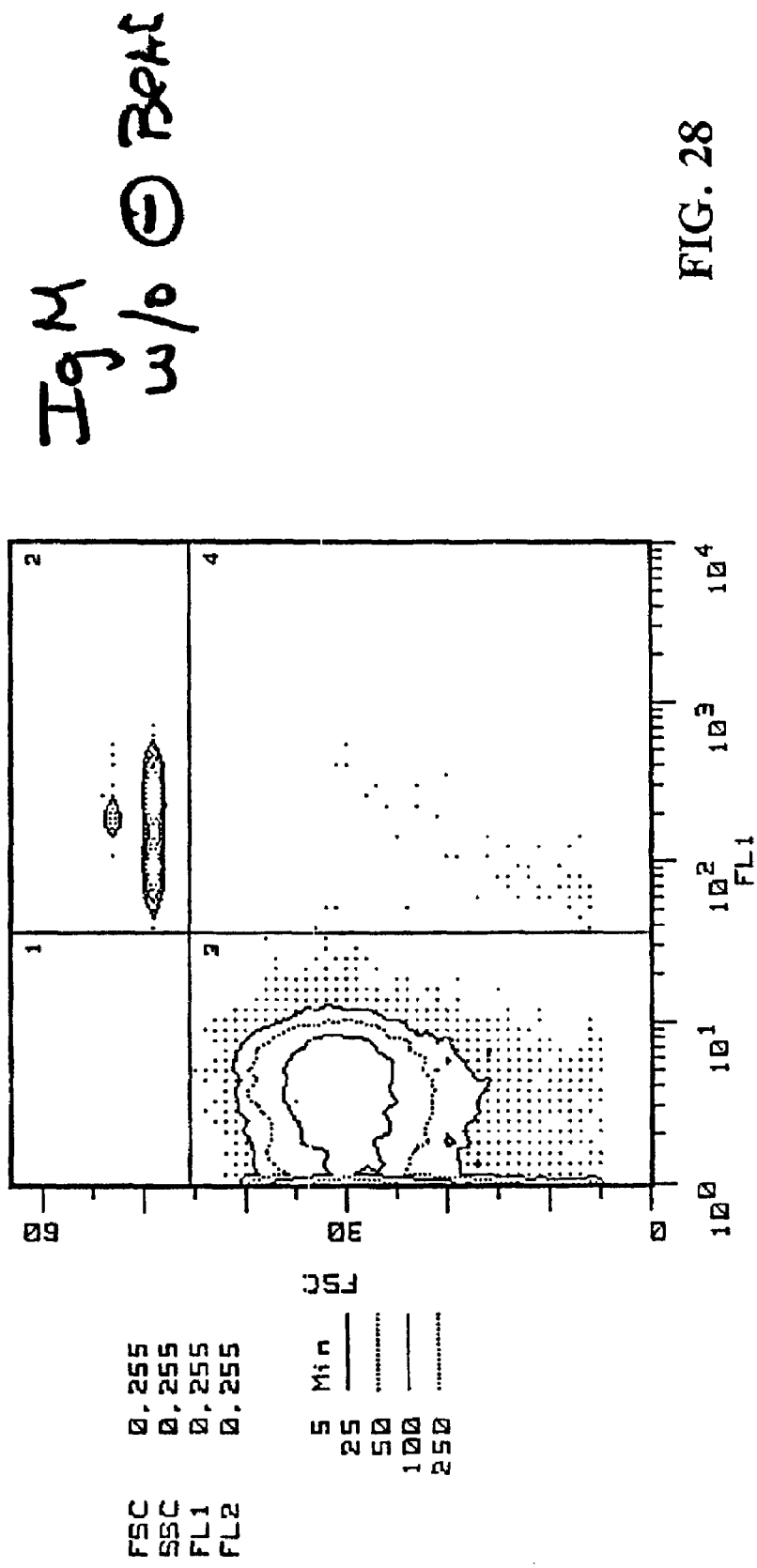
Figure 29A:
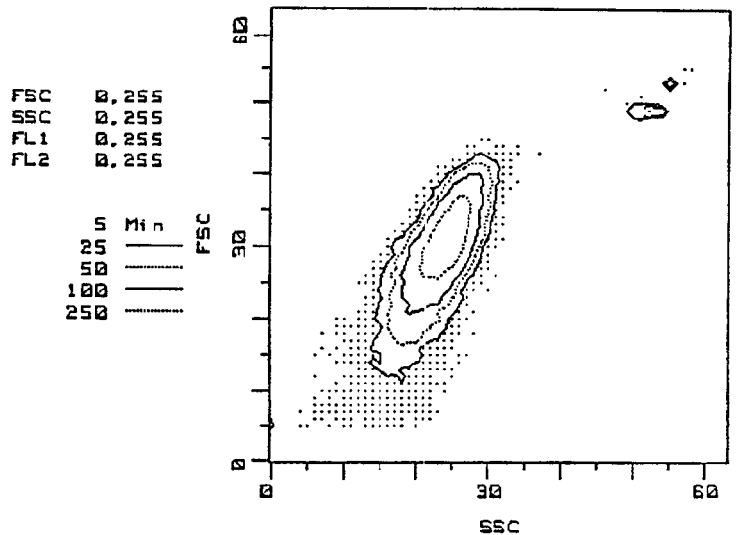
Figure 30:
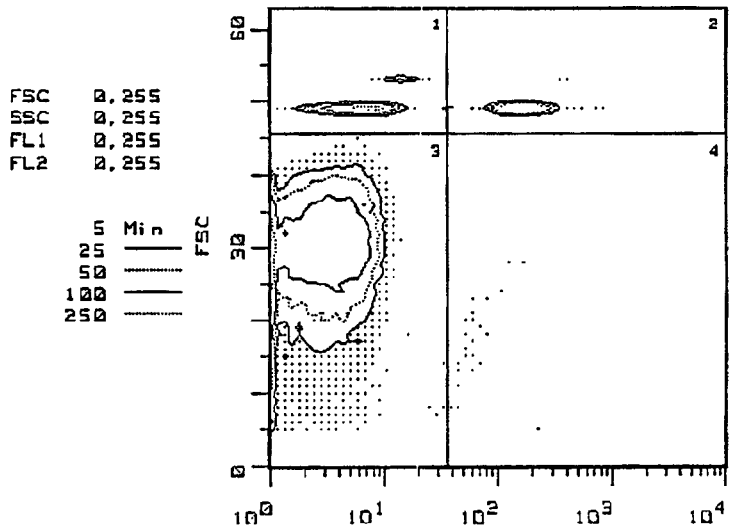
Figure 29B:
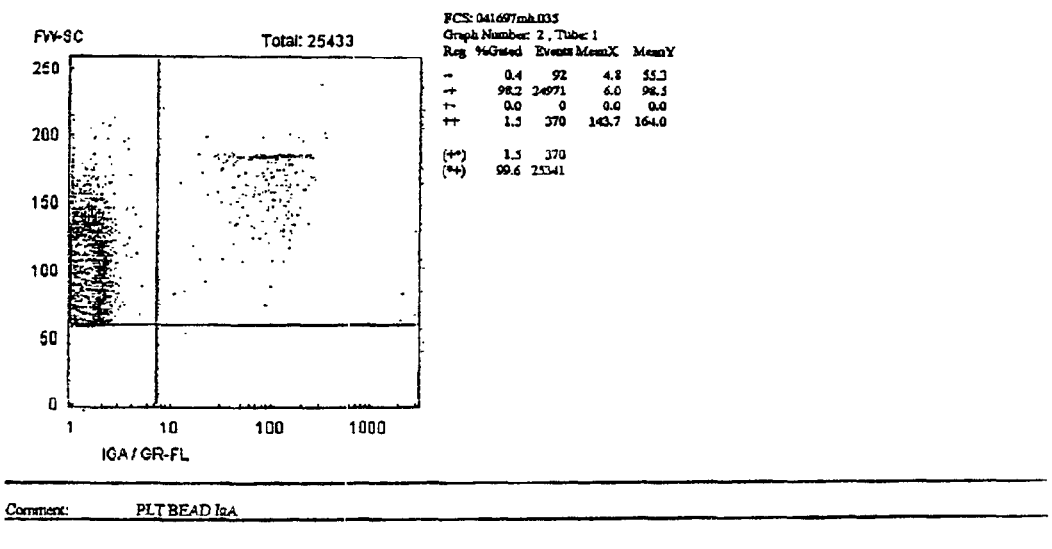
Figure 31:
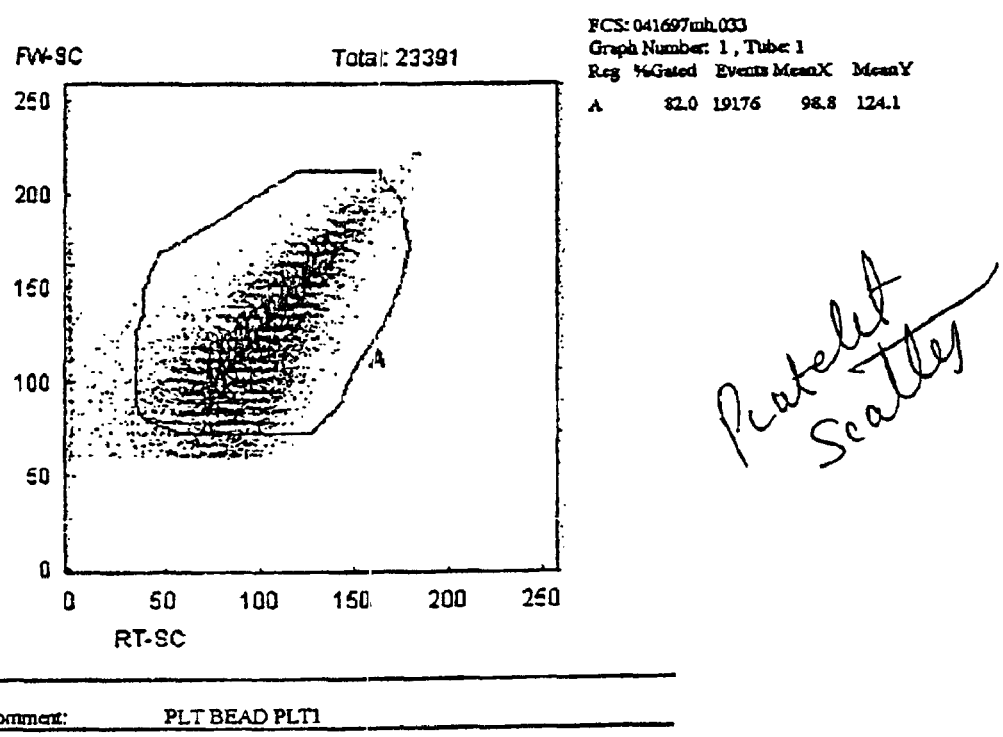
Figure 31B:
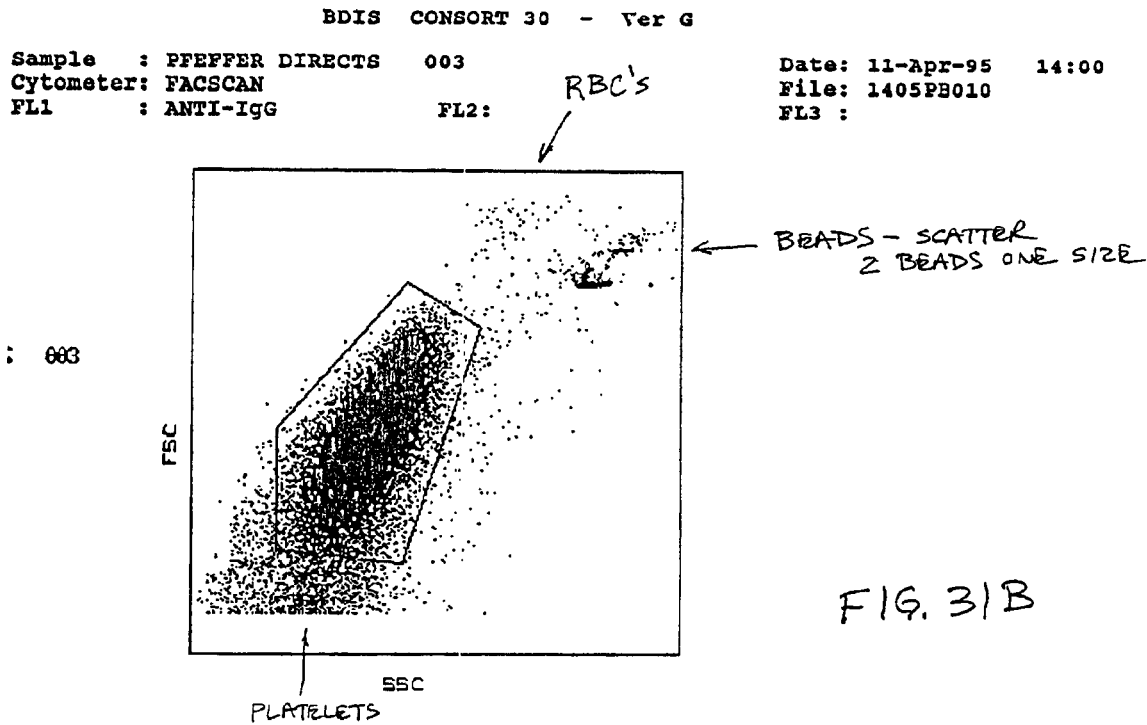

One basic principle of the present invention is to conjugate different antigens or antibodies to the exterior of latex microspheres (beads) of different sizes and to add platelets. The coated microspheres are used to detect the appropriate specific antibodies and/or antigens simultaneously in one tube and provide a positive control for each patient. The ability to detect multiple analytes in one reaction tube eliminates the variability often seen in results arising from separate assays. Procedurally, latex beads are coated with specific control antigens or antibodies. These beads may vary in size and may also contain fluorescent dyes e.g. FITC, PE, etc. One or more of these precoated beads are then incubated with the sample (serum, body fluid) solution including platelets. If an antibody-antibody or antigen-antibody complex has been formed, a 2° indicator fluorochrome labeled antibody will bind to the appropriate bead (FIG. 26).

Figure 22:
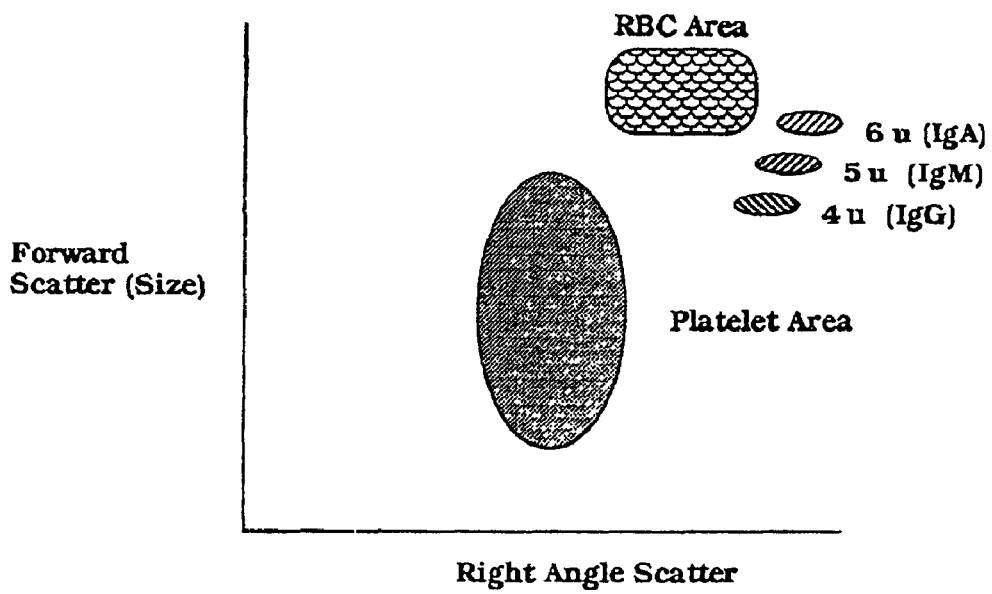
FIGS. 22–24 and 32 are schematic graphical illustrations of flow cytometer results, histograms or cytograms relating to a platelet positive control assay and reagent.

The beads/platelet mixture is centrifuged, washed, and analyzed with a flow cytometer using forward angle light scatter to discriminate the beads from platelets, and using fluorescence to detect the presence and quantity of antibodies found on the platelet and bead surfaces. The solution containing beads/platelets is passed through a series of tubes until it reaches the optical quartz cell of the flow cytometer. Because of the laminar flow of sheath fluid, single particle analysis is achieved. The signal is converted from analog to a digital display representing the size of the spheres and fluorescence of each (FIG. 24A). Controls are used to adjust for the fluorescence background created by electronic and particle noise (FIGS. 22, 23A, and 24A). A forward scatter (size) adjustment of the multiple sized bead antigen or antibody complexes is necessary in order to semi-quantitate or quantitate the relative concentration of antigen or antibody on the bead surface through single screen, visual distribution. As seen in FIG. 23A, a fluorescent threshold (x-axis) is established below which fluorescence values are considered negative. Upon addition of a "positive" sample, (containing appropriate platelet, antibody or antigen), the reaction between the fluorochrome labeled indicator antibody-antigen or antibody-antibody bead complex, amplifies the fluorescence signals detected by the flow cytometer (FIG. 24A). Thus, the definition of "positivity" in this system is relative to the negative control (background) and can easily be interpreted.

Figure 24A:
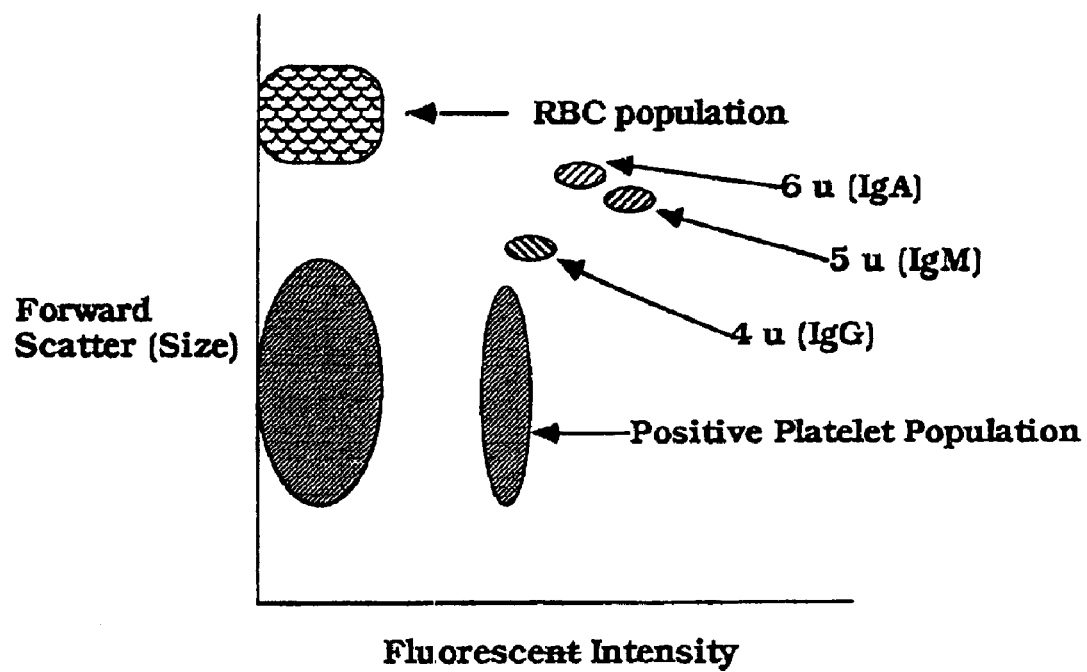
Figure 24B:
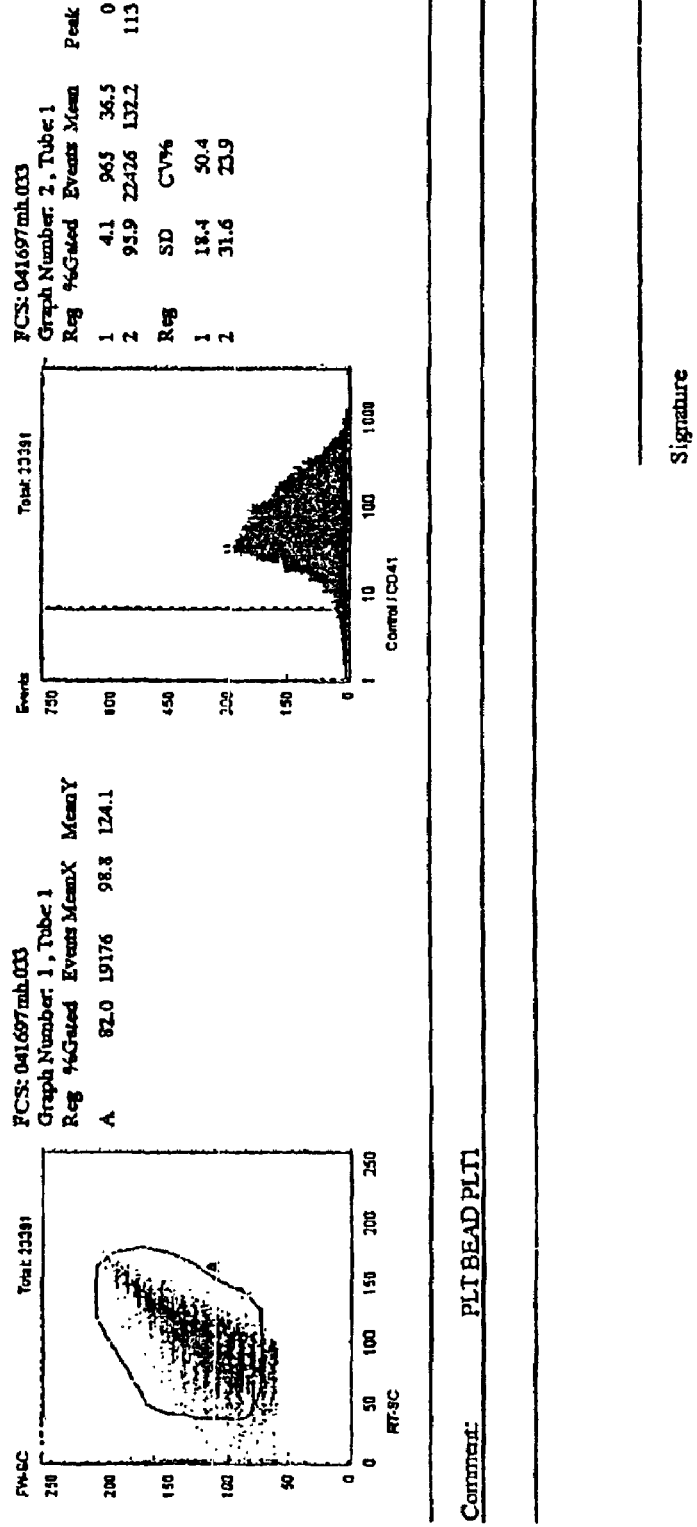
Figure 25A:
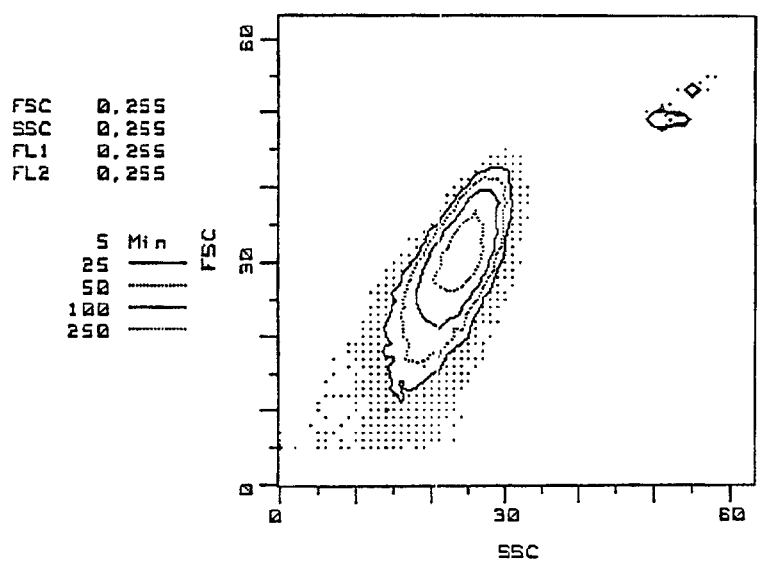

Multiple analytes including antibodies or antigens can readily be displayed and quantitative values obtained in a single two-dimensional histogram. Indices may be established by using the mean channel fluorescent value of the control (negative) and dividing it into the mean of the positive (patient) sample. Similarly, additional bead systems can be combined within the size distinguishing capabilities of the flow cytometer and the sizes available from vendors providing latex particles. As seen in FIG. 24, the multiple antigen or antibody coated bead system incorporates specific anti-species specific 2° antibodies, labeled with fluorochromes (e.g., FITC, PE, etc.), to detect the presence of antigen-antibody or antibody-antibody complexes on the beads. All other antibodies non-specifically bound to the latex surface are either washed away or ignored by the indicator antibody. At times, protein blocking may be necessary in either situation.

The present invention uses the principles of flow cytometry and light scatter to detect different sizes of latex particles and platelets with fluorescence as the endpoint. Multiple analytes including antigens or antibodies and platelets in body fluids are detected simultaneously in a single tube because each specific analyte is differentiated by the size of the bead it is bound to and platelets are differentiated by their size.

EXAMPLE 4
Double Wash Positive Control Detection System

In accordance with one example of the present invention, five distinct latex beads each coated with a unique control antigen are incubated with positive antibody control serum and then labeled with goat anti-human FITC labeled antibodies. Positivity is distinguished or semi-quantitated using uncoated negative control beads as the negative standard. Forward scatter (forward angle light scatter, FALS, size) versus green fluorescence (FL1) are used to detect positivity.

Materials

4 μm particle sized latex bead
5 μm particle sized latex bead
6 μm particle sized latex bead
7 μm particle sized latex bead
3 μm particle sized latex bead
PSA Complex antigen
CA-125 antigen
CA 27.29 antigen
CEA antigen
ERP/PRP
anti-PSA, positive sera
anti-CA-125, positive sera
anti-CA-27.29, positive sera
anti-CEA (La), lyophilyzed, positive sera
anti-ERP/PRP 70, lyophilyzed, positive sera
Goat anti-human IgG F(ab')$_2$-FITC, Tago, Inc., Cat #4200
Sodium Carbonate, Sigma Chemical, Cat # S-6139
Sodium Bicarbonate, Baker Chemical, Cat # 3506-1
Albumin, bovine, Sigma Chemical, Cat # A-7888
200 μl adjustable pipettor
pipettor tips
10 mL pipettes
Centrifuge
12×75 mL polystyrene test tubes
13 mm caps
flow cytometer
   Reagents
Carbonate Buffer, pH 9.6
1. Add 1.5 g of sodium carbonate and 0.8 g of sodium bicarbonate to 500 mL of distilled water.
2. Mix for 5–10 minutes or until all crystals are dissolved.
3. Adjust pH to 9.6 using 2N NaOH.
4. Store at 4–8° C.
5. Buffer only to be used for less than 48 hours after preparation. For antigen coating only.
0.5% albumin, bovine in PBS
1. Mix 0.5 g of bovine albumin in 100 mL of PBS.
2. Mix thoroughly.
3. Store at 4–8° C. for one month.
   Procedure
1. Determine the amount of latex bead suspension (e.g. # of drops/mL carbonate buffer) needed to achieve an event count of 900–1000 beads/second on the flow cytometer.
2. Titer control antigen (Ag) to appropriate μg/mL and use concentration deemed optimal for maximum mean channel and fluorescence.
3. Add antigen to each respective tube: (μg)

| Antigen (size bead) | Drops/mL Buffer | Ag/mL Buffer |
|---|---|---|
| PSA (4 μm) | 1–20 | 1–50 |
| CA-125 (5 μm) | 1–20 | 1–50 |
| CA27–29 (6 μm) | 1–20 | 1–50 |
| CEA (7 μm) | 1–20 | 1–50 |
| ERP/PRP-70 (10 μm) | 1–20 | 1–50 |

4. Incubate bead/antigen mixture for 12–20 hours at 4–8° C.
5. Centrifuge solution at full speed in a refrigerated centrifuge for 10 minutes.
6. Decant supernatant and gently resuspend beads by hand.
7. Add 1 mL of 0.1–0.5% albumin in PBS per mL original volume.
8. Gently vortex.
9. Repeat steps 5 and 6.
10. Add 1 mL of carbonate buffer per original milliliters of antigen/bead solution.
11. Add 100 μL of each antigen/bead mixture to all reaction tubes.
12. Add 50 μL of each positive serum diluted to appropriately labeled tube.
13. Vortex gently and incubate for 15 minutes at room temperature.
14. Wash once with 1 mL carbonate buffer.
15. Repeat steps 5 and 6.
16. Add 20 μL of Goat anti-human IgG F(ab')$_2$-FITC 1:20 (NOTE: dilution may slightly vary from lot to lot. Titer all new lots).

17. Gently vortex and incubate 15 minutes at room temperature.
18. Repeat steps 5 and 6.
19. Add 1.0 mL of carbonate buffer.
20. Read on flow cytometer.

EXAMPLE 5
Double Wash Positive Control Detection System

In accordance with another example of the present invention, an immunobead-flow cytometry method for simultaneously detecting a plurality of antigens and platelets is as follows.

Procedure
1. Determine the amount of latex bead suspension (e.g. # of drop s/mL carbonate buffer) needed to achieve an event count of at least 500 beads/second on the flow cytometer.
2. Titer positive control antigen (Ag) to appropriate µg/mL and use concentration deemed optimal for maximum mean channel and fluorescence.
3. Add antigen to each respective tube: (µg)

| Antigen (size bead) | Drops/mL Buffer | Ag/mL Buffer |
|---|---|---|
| IL-2 (0.25 µm) | 1–3 | 5–60 |
| IL-4 (0.50 µm) | 1–5 | 5–60 |
| IL-20 (0.75 µm) | 2–10 | 5–60 |
| TNP (1.0 µm) | 2–10 | 5–60 |
| FaL.C. (1.25 µm) | 3–20 | 5–60 |

4. Incubate bead/antigen mixture for 12–24 hours at 4–8° C.
5. Centrifuge solution at full speed in a refrigerated centrifuge for 10 minutes.
6. Decant supernatant.
7. Gently resuspend beads by hand.
8. Gently vortex.
9. Repeat steps 5 and 6.
10. Add 1 mL of carbonate buffer per original milliliters of antigen/bead solution.
11. Add 100 mL of each antigen/bead mixture to all reaction tubes.
12. Add 500 µL of the 5 antigen-coated bead suspension.
13. Add 50 µL of patient or control sera.
14. Gently vortex and incubate for 15 minutes at room temperature.
15. Make a 1:5 dilution of Goat anti-human F(ab')$^2$ IgG-FITC in PBS.
16. Add 50 µL of diluted conjugate to the bead suspension.
17. Incubate for 15 minutes at room temperature in the dark.
18. Add 1 mL of PBS.
19. Analyze on flow cytometer.

Cytometer adjustments of fluorescent gains will change, therefore, it is recommended that a blank and positive control be run as reference material. Conjugate titers may vary, serial dilutions must be made on all new lots.

EXAMPLE 6
Double Wash Control Detection System

In accordance with another example of the present invention the multiple parameter bead assay is as follows.

Procedure
1. Determine the amount of latex bead suspension (e.g. # of drop s/mL carbonate buffer) needed to achieve an event count of 900–1000 beads/second on the flow cytometer.
2. Titer positive control immunoglobulin (Ig) to appropriate µg/mL and use concentration deemed optimal for maximum mean channel and fluorescence.
3. Add positive control Ig to each respective tube: (µg)

| Ig (size bead) | Drops/mL Buffer | Ig/mL Buffer | Dilution |
|---|---|---|---|
| IgG (4 µm) | 2–10 | 5–40 | 1:0–1:400,000 |
| IgA (6 µm) | 6–12 | 10–100 | 1:10–1:600000 |
| IgM (8 µm) | 4–20 | 10–100 | 1:5–1:600000 |

4. Incubate bead/Ig mixture for 12–24 hours at 4–8° C.
5. Centrifuge solution at full speed in a refrigerated centrifuge for 10 minutes.
6. Decant supernatant.
7. Gently resuspend beads by hand.
8. Gently vortex.
9. Repeat steps 5 and 6.
10. Add 1 mL of carbonate buffer per original milliliters of Ig/bead solution.
11. Add 100 µL of each Ig/bead mixture to all reaction tubes.
12. Dilute positive serum 1:20 in PBS.
13. Add 50 µL of each Type O control or patient platelets to appropriately labeled tube.
14. Vortex gently and incubate for 15 minutes at room temperature.
15. Wash once with 1 mL Isotonic saline.
16. Repeat steps 5 and 6.
17. Add 50 µL of Goat anti-human IgG F(ab')$^2$-FITC 1:20 (NOTE: dilution may slightly vary from lot to lot. Titer all new lots).
18. Gently vortex and incubate 15 minutes at room temperature.
19. Repeat steps 5 and 6.
20. Add 1.0 mL of Isotonic saline.
21. Read on flow cytometer.

It has been demonstrated that immunoglobulin (Ig) can be attached to latex beads (FIGS. 25–30). After incubation with fluorescenated anti-human Ig and/or platelets, beads that have bound antibody fluoresce and/or platelets are specifically detectable because of their size differences (FIGS. 22–31).

The results of the control assays of the present invention are improved by determining: 1) optimal concentrations of analytes including antigens, antibodies or Ig on latex microspheres using block titration methods; 2) optimal ratios of serum or platelets to bead concentrations; and 3) optimal concentrations of secondary antibody (anti-human Ig). Once optimal bead, analyte, antigen, antibody, and/or platelet concentrations are determined and, using commercially available control analytes, antigens, antibodies, Ig, platelets, and patient platelets sera containing these analytes, antibodies, antigens, platelets coated beads are incubated with various dilutions of sera, platelets and secondary (detector) antibody. Several dilutions of known positive sera and platelets can be performed to determine the sensitivity of the assay for each patient.

Further, replicates should be performed on an automated system, e.g. the Becton Dickinson Calibin with an autoloader, to determine reproducibility. Stability of analytes, reagents, coated beads, etc. is determined by a longitudinal study in which they are tested for reactivity to the same sera at monthly intervals for at least six months.

Each FIBA-FCM assay kit of the present invention should be tested in multiple clinical flow cytometry laboratories, using the same positive and negative sera and platelets to determine inter-laboratory variation.

Figure 8:
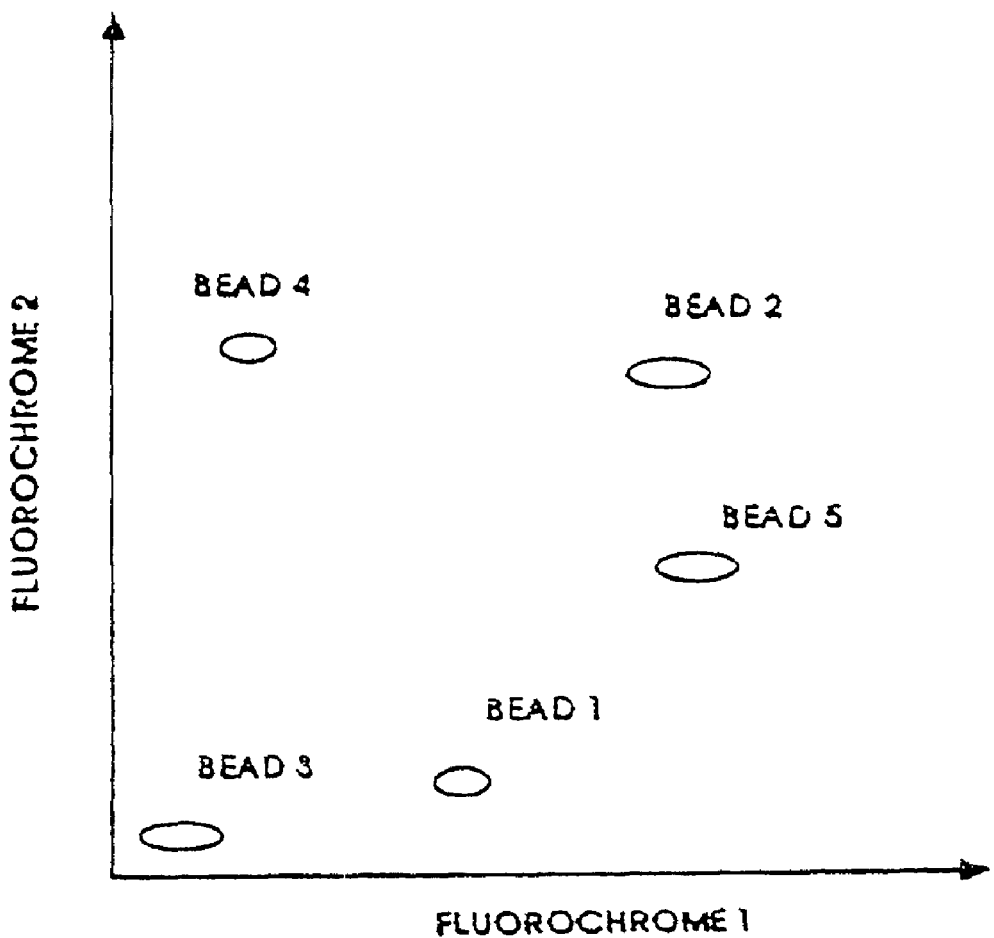
FIG. 8 is a schematic representation of a two dimensional flow cytometer histogram of different sized beads labeled with different fluorochromes.
Figure 9:
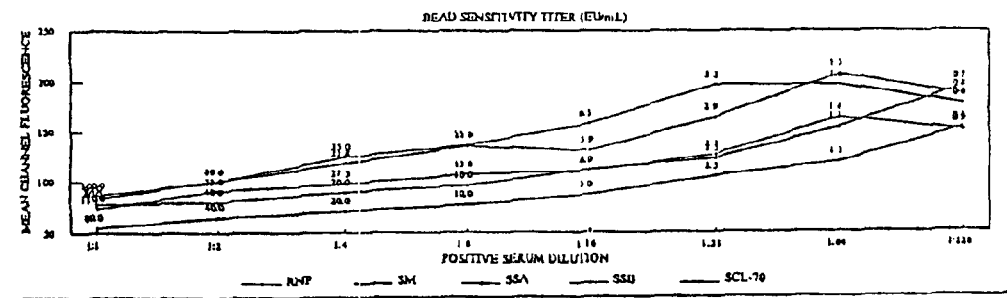
FIGS. 9–21 and 25–31 are graphical and tabular representations of flow cytometer results, histograms or cytograms relating to platelets, reagents and assays.
Figure 10:
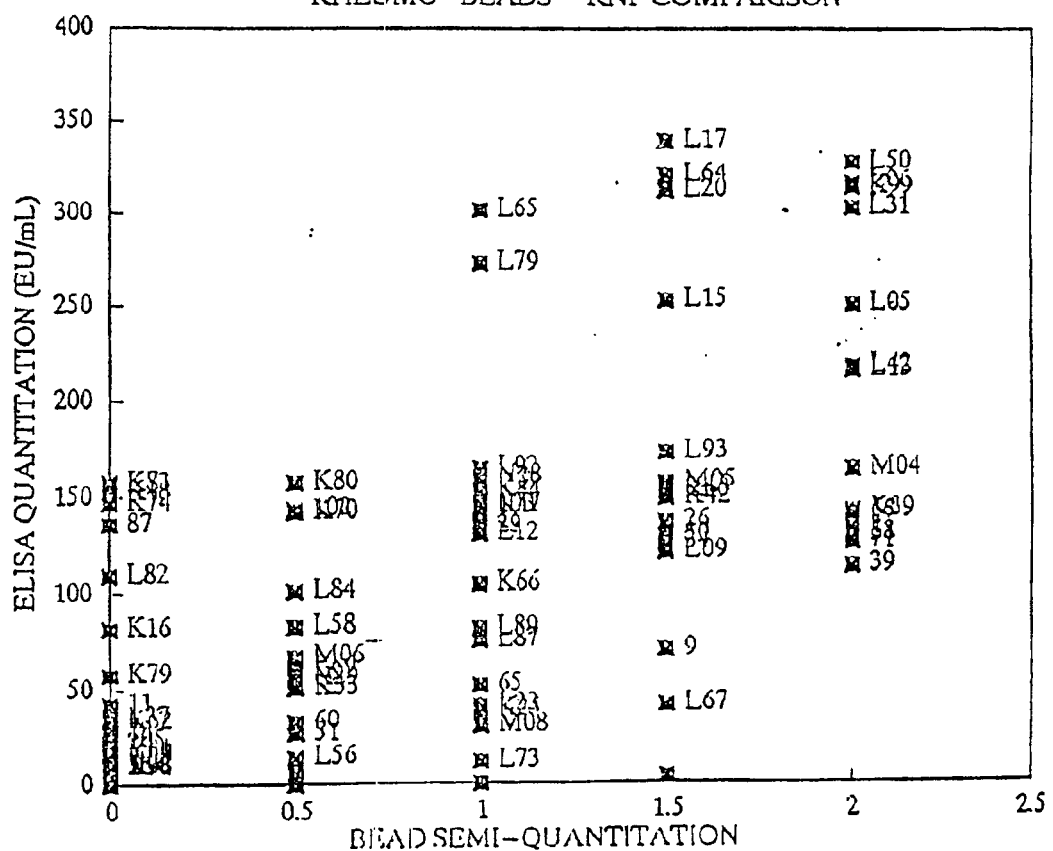
Figure 11:
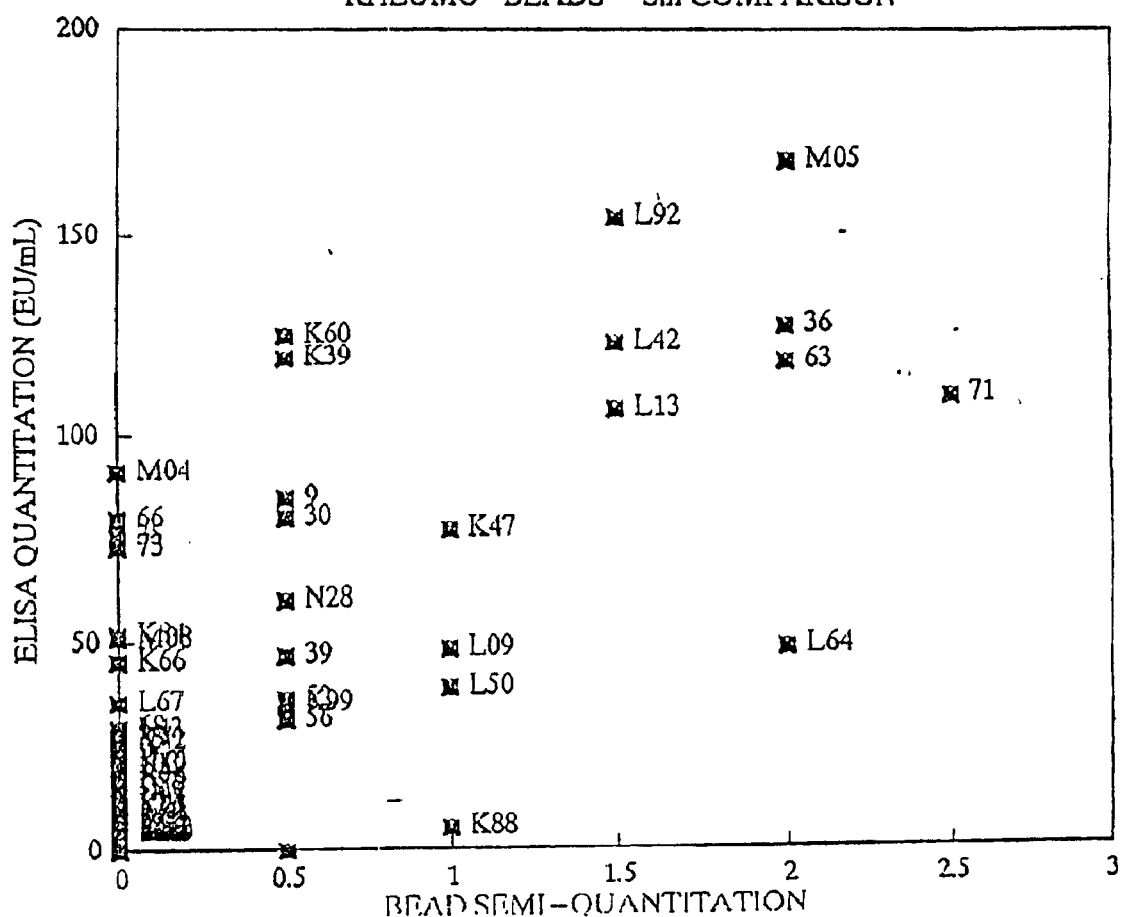
Figure 12:
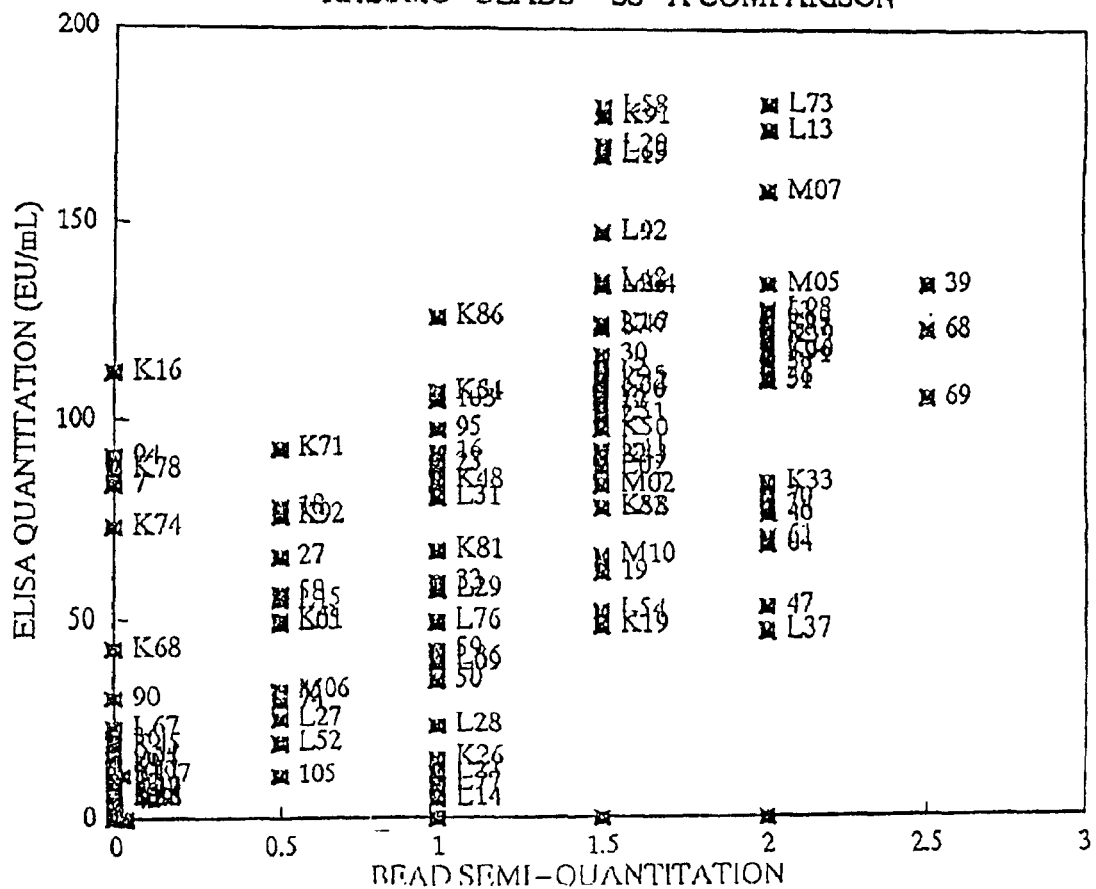
Figure 13:
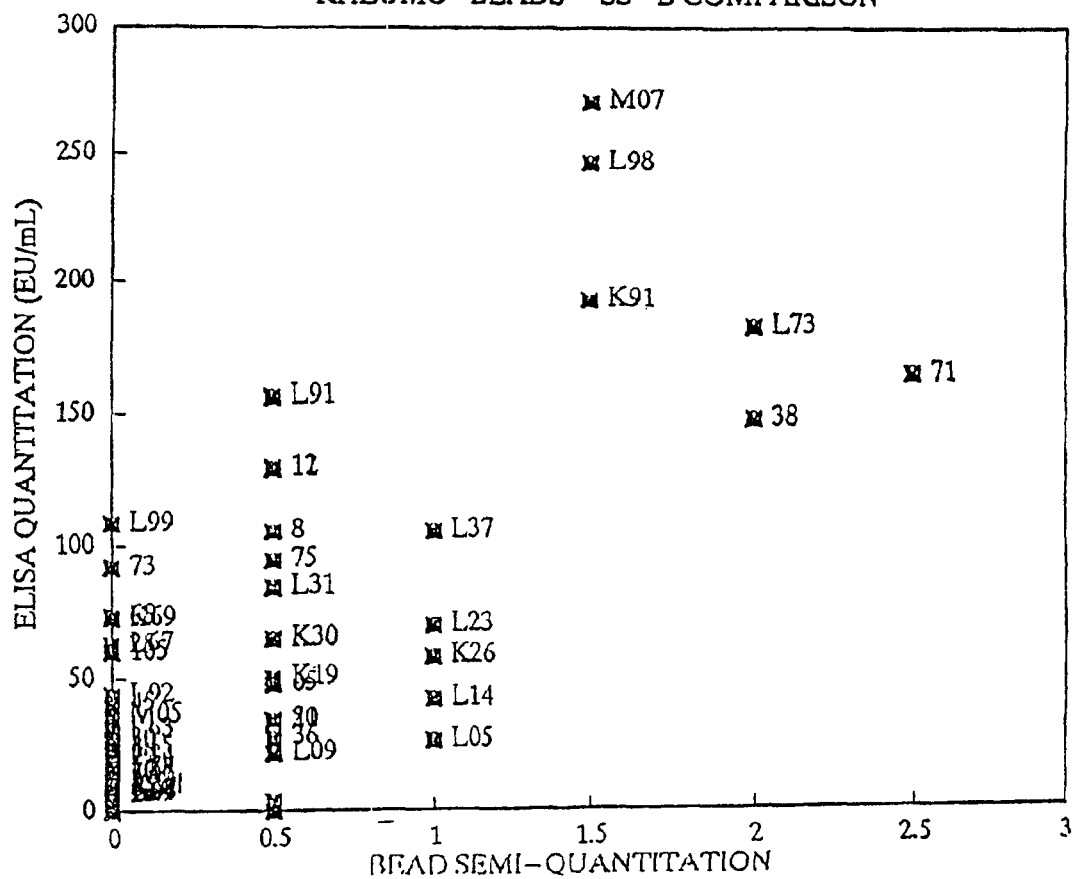
Figure 14:
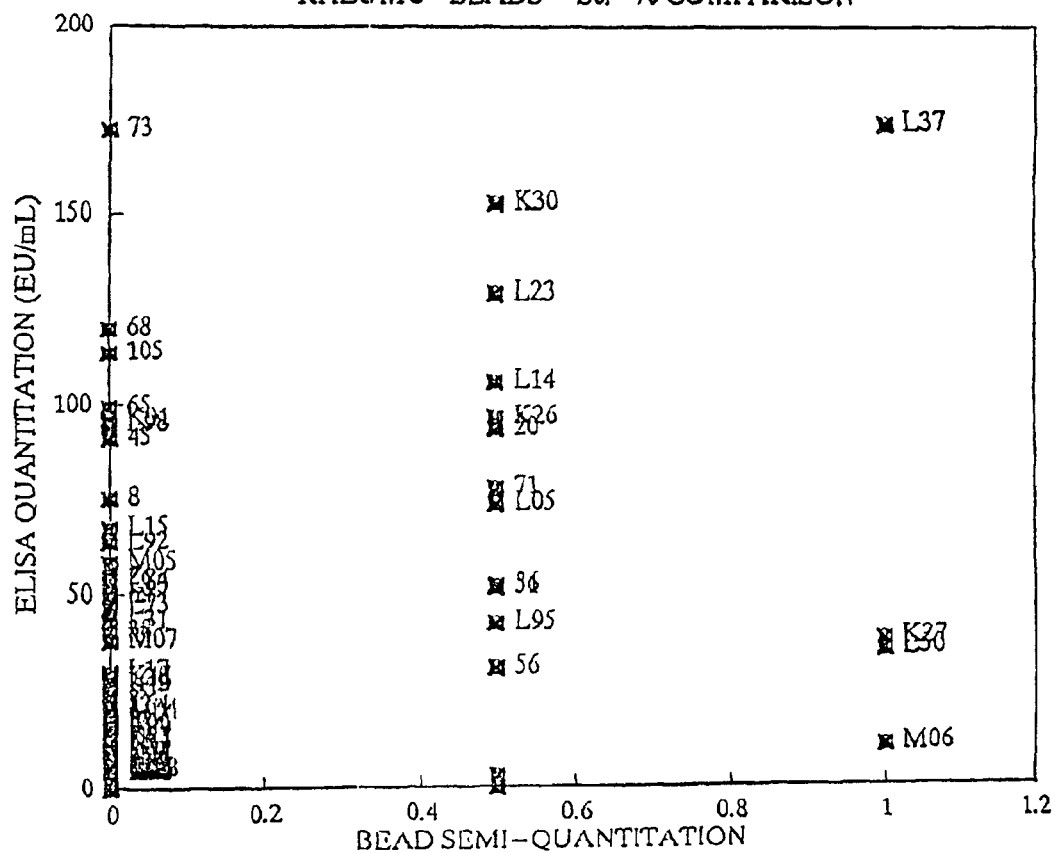
Figure 15:
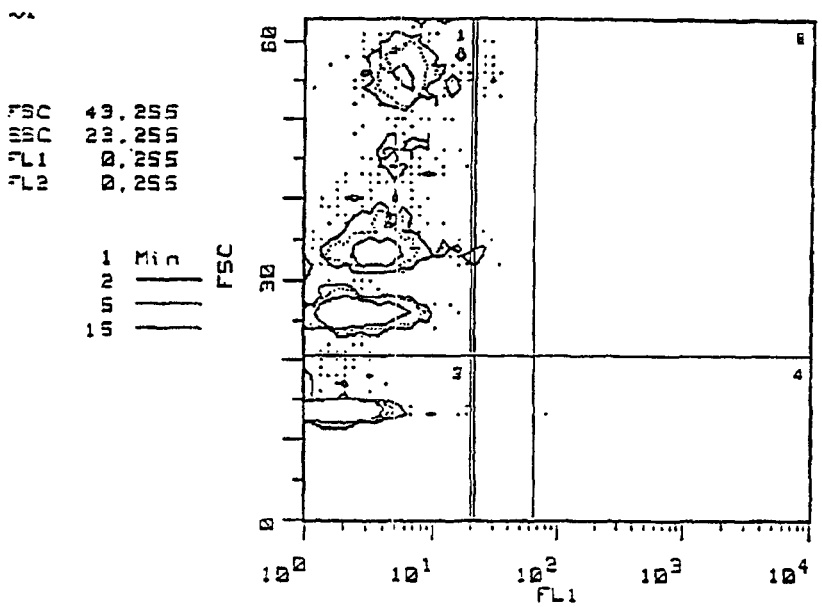
Figure 16:
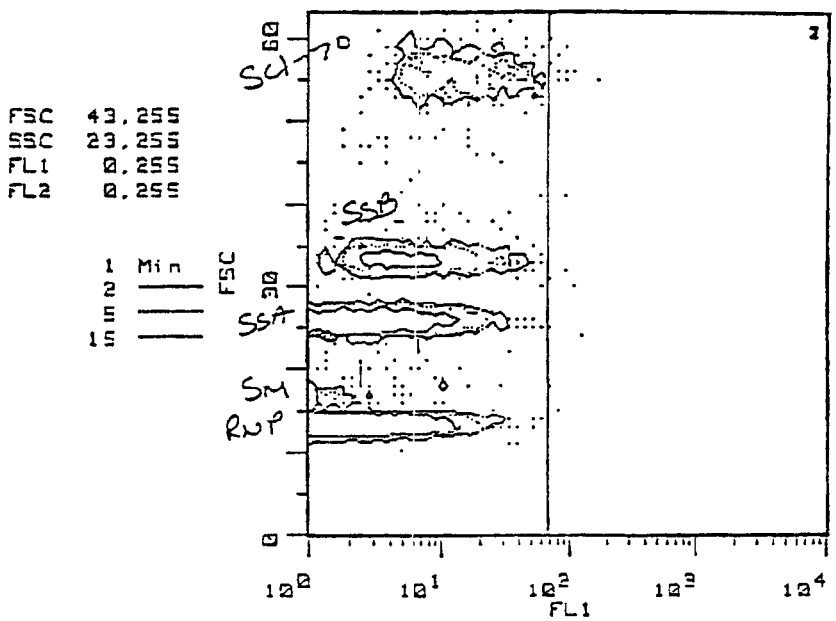
Figure 17:
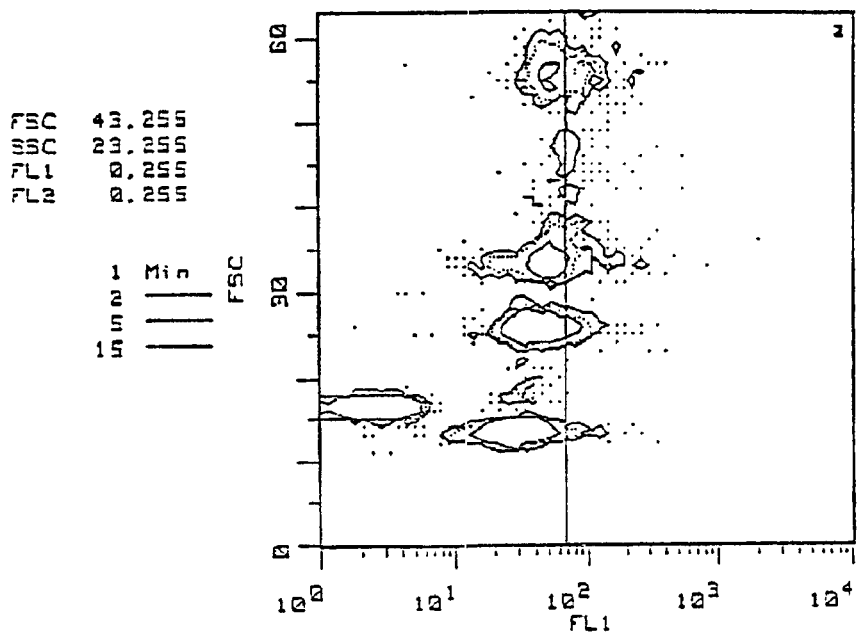
Figure 18:
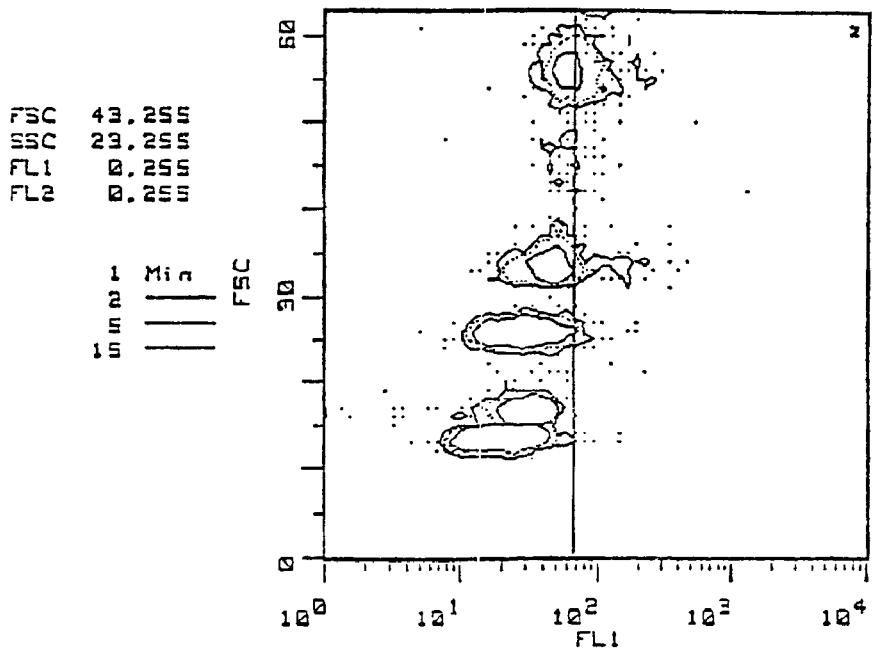
Figure 19:
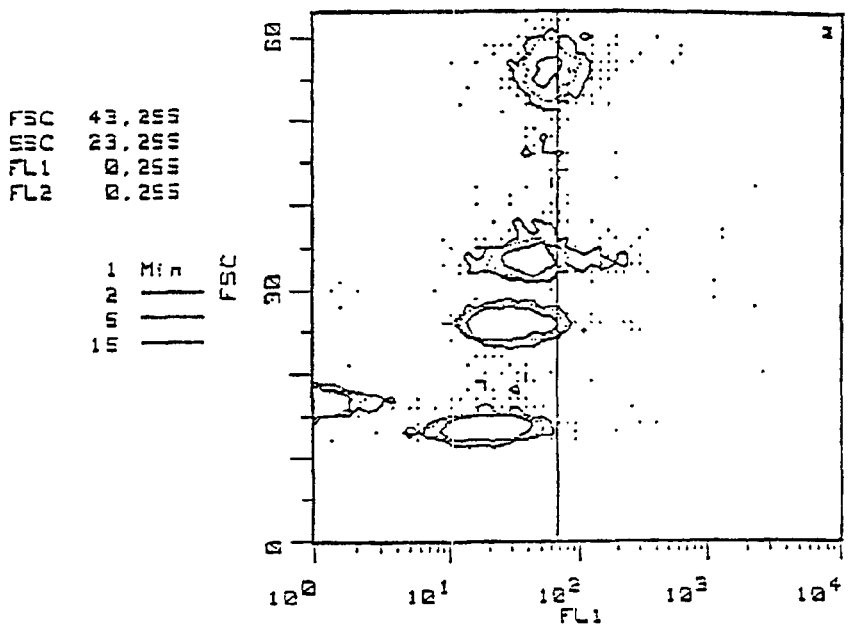
Figure 20:
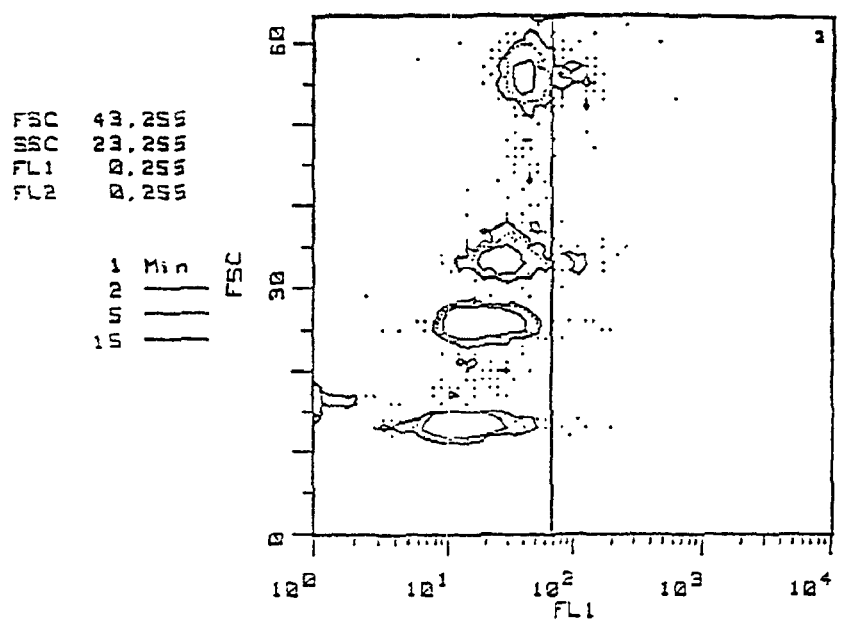
Figure 21:
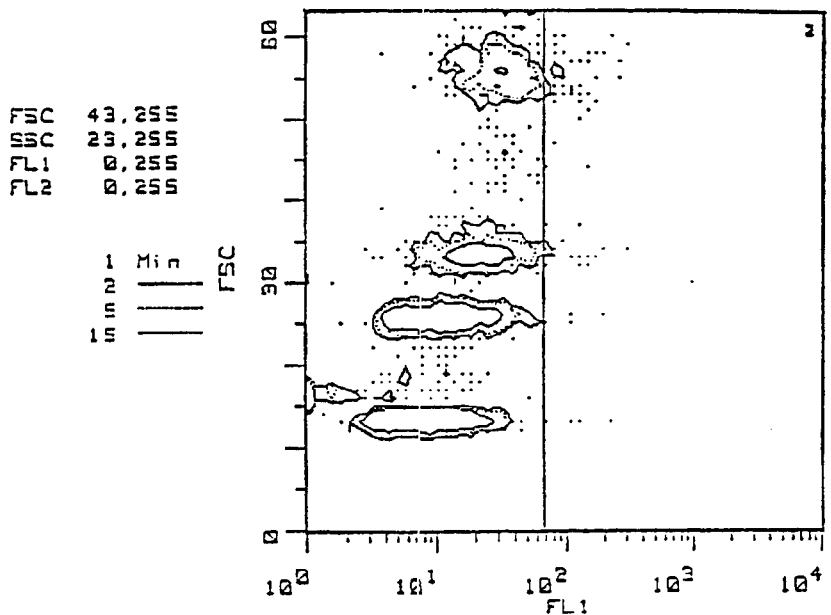

The positive control methodology of the present invention provides that platelets and microsphere sizes can be combined with two color FCM and results displayed three dimensionally as a "cloud" display. This increases the number of analytes, platelets, antibodies or antigens to be simultaneously analyzed (FIG. 8).

EXAMPLE 7
Multiple Parameter Control Reagent and Assay

In accordance with another embodiment of the present invention, positive control IgG, IgM, and IgA are each separately bound to micron latex beads and stabilized for extended shelf life. Then, an incubation with goat anti-human Ig, conjugated with fluorescein isothiocyanate (FITC), is carried out. This conjugate will bind immunologically to the specific Ig on the beads, forming a "sandwich" consisting of bead-Ig-2° antibody-FITC.

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into two parameter histograms expressing forward light scatter (Y-axis) versus fluorescence intensity (X-axis, FIGS. 24A and 26, 27B, 28, and 30).

Procedure
1. Determine which Ig coating buffer (either carbonate buffer or phosphate buffered saline, PBS) yields highest binding capacity to latex beads. Optimal concentration of beads needs to be determined in order for the flow cytometer to count accurately.
2. Establish titers of both Ig and antibody against the coated beads and run several experiments to maximize signals obtained at different Ig concentrations (mean channel fluorescence).
3. Incubate Ig/bead mixture for several minutes (time to be determined) and wash with either carbonate buffer or PBS.
4. Wash Ig coated beads in buffer (PBS or 0.5% Tween 20 in PBS or carbonate buffer).
5. Determine the background of unlabelled beads.
6. If background exists, decrease to near baseline values.

EXAMPLE 8
Multiple Parameter Control System

In accordance with one embodiment of the present invention, one or more control antigens are bound to one or more $\mu$m latex beads, respectively and stabilized for extended shelf life. Diluted control serum is placed into test tubes containing a mixture of the control antigen coated beads and incubated. If a control antibody is present for a specific antigen, it will bind to that specific bead. After washing the control bead/serum mixture, a second incubation with anti-human Ig, conjugated with fluorescein isothiocyanate (FITC), is carried out. This conjugate will bind immunologically to the anti-antigen Ig of the antigen-antibody complex, forming a "sandwich" consisting of bead-antigen-1° antibody-20 antibody-FITC (FIG. 1).

Unbound conjugate is removed in the subsequent washing step. Patient or control platelets can be added. The fluorescence intensity is based on the avidity of the bead/antibody/conjugate binding. The control samples are analyzed using flow cytometers having laser excitation wavelengths of 488 nm. Emission wavelengths of 514 nm are detected by photomultipliers which convert the fluorescent analog signals into at least two parameter histograms expressing forward light scatter (Y-axis) versus fluorescence intensity (X-axis, FIG. 2).

EXAMPLE 9

In accordance with another embodiment of the present invention, a "no wash" control immunoassay or immunobead-flow cytometry, control antigens, antibodies, and/or Ig are bound to different or same sized $\mu$m latex beads, respectively and stabilized for extended shelf life. Diluted control serum is placed into the test tubes containing the coated beads and incubated. If an antibody is present for a specific antigen, antibody or Ig, it will bind to that specific bead. Next, a conjugated indicator antibody is added to all tubes and a second incubation is carried out. This secondary antibody will bind immunologically to the anti-antigen Ig of the antigen-antibody complex, or Ig forming a "sandwich" consisting of bead-antigen-1° antibody-conjugated 2° antibody-(FIG. 1) or bead-Ig-conjugated antibody-FITC. Control or patient platelets are added to respective tubes. Then, saline is added and the samples are analyzed on a flow cytometer.

EXAMPLE 10
One Step No Wash Control System

The following "no wash" procedure is a modification of the above bead evaluation method.
1. Allow reagents to come to room temperature.
2. Gently invert antigen, antibody, Ig, bacteria, virus, or other analyte coated bead mixture until an even distribution of bead product is observed.
3. Label test tubes for Blank, Controls, and Patients.
4. Add 100 $\mu$L of each bead suspension to each tube.
5. Add 50 $\mu$L of serum to appropriate test tubes.
6. Add 50 $\mu$L of negative serum to internal control tube.
7. Gently vortex and incubate for 15 minutes at room temperature.
8. Make a 1:20 dilution of goat anti-human F(ab')$^2$ Ig FITC (or other fluorochrome (dilution may vary from lot to lot).
9. Add 50 $\mu$L of diluted conjugate to each tube.
10. Add patient platelets or control platelets to appropriate test tubes.
11. Gently vortex and incubate for 15 minutes at room temperature, in the dark.
12. Add 1 mL of saline to each tube.
13. Analyze on flow cytometer.

EXAMPLE 11
No Wash Control System
1. Allow reagents to come to room temperature.
2. Gently invert Ig coated bead mixture until an even distribution of bead product is observed.
3. Label test tubes for Blank, Positive Control, and Negative Control, and product.
4. Add 10–100 $\mu$L of each bead suspension to each tube.
5. Add 10 $\mu$L of platelets to appropriate test tubes.
6. Add at least 10 $\mu$L of Saline to blank tube.
7. Gently vortex and incubate for at least 15 minutes at room temperature.
8. Make an at least 1:2 dilution of labeled anti-human Ig antibodies in PBS.
9. Add at least 10 $\mu$L of diluted conjugate to each tube.
10. Gently vortex and incubate for at least 5 minutes at room temperature, in the dark.
11. Add about 1 mL of saline to each tube.
12. Analyze on flow cytometer.

EXAMPLE 12
No Wash Control System
1. Allow reagents to come to room temperature.
2. Gently invert Ig coated bead mixture until an even distribution of bead product is observed.

3. Label test tubes for Blank, Positive Control, and Patient Control.
4. Add equal quantities of bead suspension to each tube.
5. Dilute patient and control platelets to about 1:20 in saline (e.g. 10 μL platelets to 190 μL saline).
6. Add equal quantities of diluted platelets to appropriate test tubes.
7. Add the same quantity of PBS to blank tube.
8. Gently vortex and incubate at room temperature.
9. Make an about 1:5 dilution of conjugated anti-human antibody in PBS.
10. Add equal quantities of diluted conjugate to each tube.
11. Gently vortex and incubate at room temperature.
12. Add equal quantities of PBS to each tube.
13. Analyze on flow cytometer.

EXAMPLE 13
Anti-SLE Positive Control

In accordance with still another embodiment of the present invention, an FIBA-FCM assay positive control is described as follows.

Summary of Procedure
1. Add 50 μL of control serum (human antibodies against the selected antigens) to 600 μL of RNP, Sm, SS-A(Ro), SS-B(La), dsDNA and Scl-70 coated bead solution. Mix well.
2. Incubate at room temperature for 15 minutes.
3. Place one drop (approx 50 ml) of fluorescenated conjugate into each tube. Mix well.
4. Incubate at room temperature, in the dark, for 15 minutes.
5. Read on flow cytometer.

Intended Use Of Positive Control

For the simultaneous detection of the positive fluorescence values of platelets and of anti-antibodies to the antibodies against the antigens RNP, Sm, SS-A(Ro), SS-B(La), dsDNA and Scl-70 in serum as an aid in the setting of the positive reading region for each patient.

EXAMPLE 14

Highly purified bacterial antigen are bound to respective different sized μm latex beads and stabilized for extended shelf life. Diluted patient's sera are placed into test tubes containing a mixture of the antigen coated beads and incubated. If an antibody is present to the specific antigen (i.e. bead), it will bind to that specific bead. After washing the bead/sera mixture to remove residual sample, a second incubation with goat anti-human Ig conjugated with fluorescein isothiocyanate (FITC) is carried out. Conjugate will bind immunologically to the anti-antigen Ig of the antigen-antibody complex, forming a "sandwich" (FIG. 1).

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into digital signals two parameter histograms size (Y-axis) versus fluorescent intensity (X-axis, FIG. 2).

EXAMPLE 15

Allow test components and patient samples to warm to room temperature before use. Return promptly to refrigerator after use.
1. Properly label sufficient numbers of test tubes to identify positive, patient and negative controls and patient samples.
2. Add 500 μL of a solution containing each bead suspension into each of the labeled test tubes.
3. Prepare appropriate dilutions of the Positive, Patient and Negative Controls, and the patient samples.
4. Mix sample dilutions gently by withdrawing and expelling in a pipette tip 2 or 3 times (microtiter plate) or vortexing.
5. Transfer 15 uL of each diluted control or patient sample into corresponding test tube.
6. Gently vortex and incubate at room temperature (20 to 30° C.) for 15 minutes.
7. Add 1 mL of control or patient platelets to appropriate test tube.
8. Centrifuge for 10 minutes at 1500 g at 2–8° C.
9. Carefully decant supernatant and gently resuspend bead pellet by hand.
10. Add one drop (50 μL) of fluorescenated conjugate to each tube.
11. Gently vortex and incubate for 15 minutes at room temperature in the dark.
12. Add 1 mL of Wash Solution to each tube.
13. Centrifuge for 10 minutes at 1500 g at 2–8° C.
14. Carefully decant supernatant and gently resuspend bead pellet by hand.
15. Add 1 mL of Wash Solution to each tube.
16. Analyze on flow cytometer.

NOTE: Analysis should be made within 2 hours of final staining.

Calculation of Results

The evaluation of specimens is based on a semi-quantitation of the fluorescent intensity. Gradations are directly related to the linear scale used on the FL1 x-axis. Samples will therefore be gated by two-parameter settings (e.g. forward angle light scatter and FL1 or FL1). Position fluorescent cursor on the x-axis in accordance with the patient control, negative control and positive control values (FIGS. 23A, 24A, 26, 28 and 30). This will determine the degree of positivity (FIG. 24A). Generally, mean channel intensity of fluorescence is used as an indicator of positivity.

Figure 23:
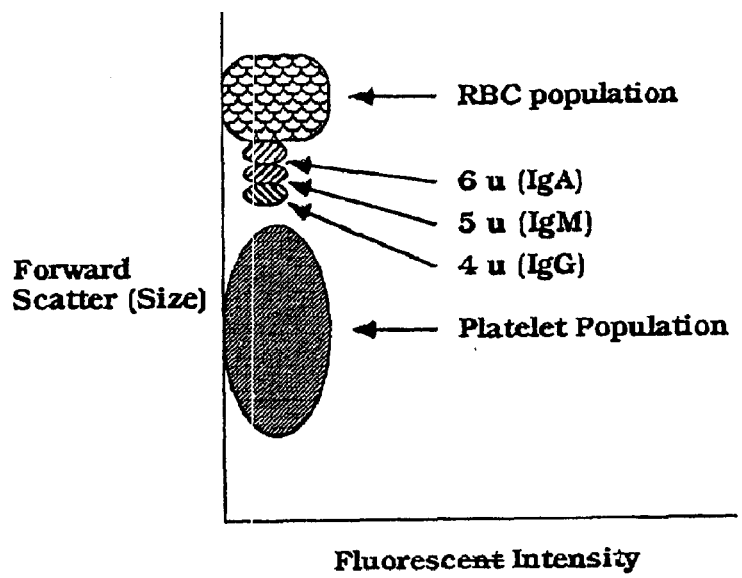
Figure 23B:
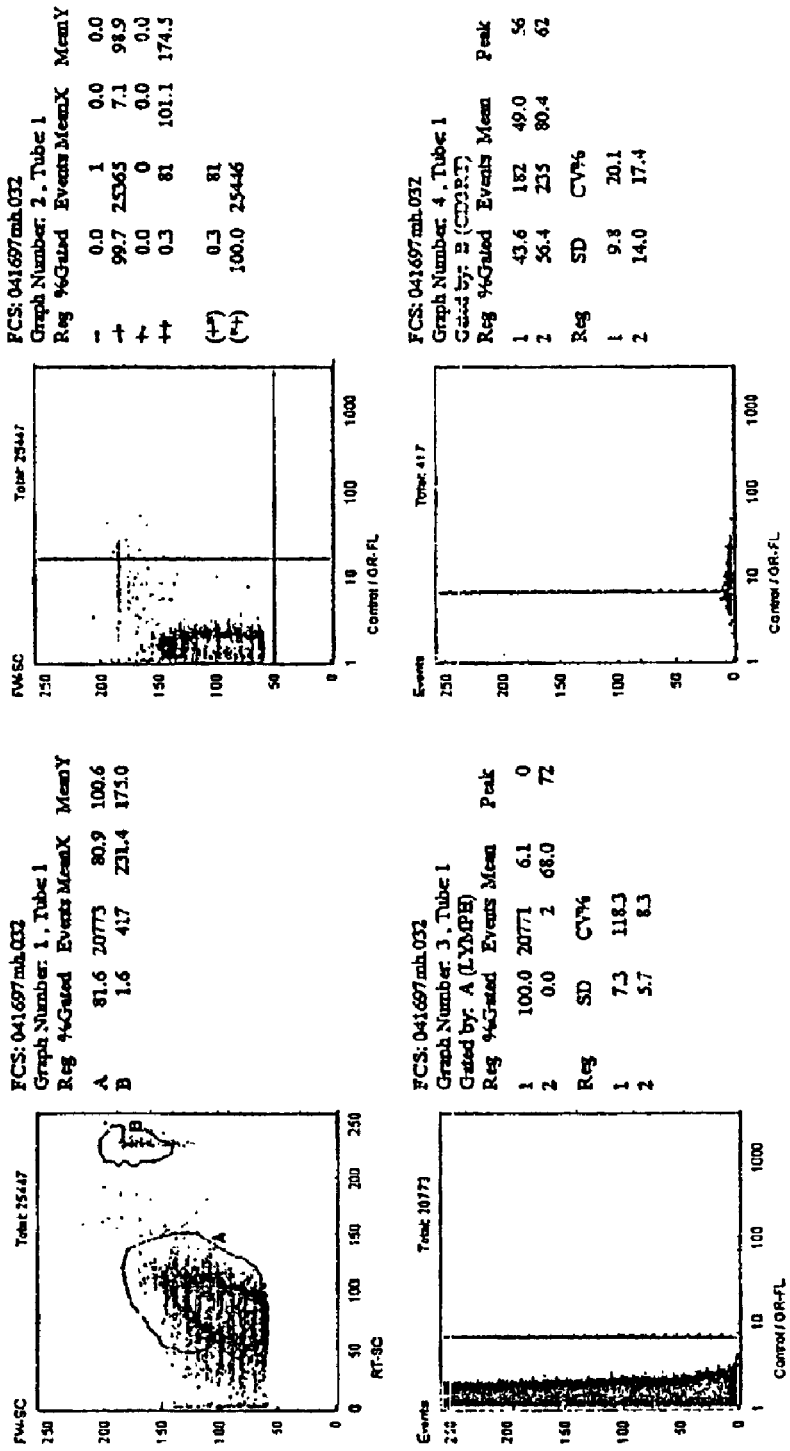

A negative control serum, when run with the assay kit, should fall within the 100 linear units of the FL1 origin (FIG. 23). Place a single vertical cursor from this point to indicate the region of positivity to the right (FIGS. 24, 26, 28 and 30).

Negative Control

All fluorescent intensity falling to the right of this region will be semi-quantitated according to the relative position on the FL1 linear scale (FIG. 23).

Test Validation Criteria
a) The Positive, Patient and Negative Controls should be included in each test run as well as a bead blank.
b) The fluorescence intensity of the Positive Control should be 1.5× mean channels or greater.
c) The Positive Control should give a semi-quantitative value within the range for that lot.

If any of these criteria are not met, the results may be invalid and the test should be repeated.

Before equivocal results are reported, retest the sample by the above described method or another approved method. Alternatively, obtain another sample from the same patient and retest.

When testing with platelets, μm beads sizes should run from about 0.25 μm to 1.5 μm and 3.5 μm to 740.0 μm.

Other bead materials used as positive controls may include, polystyrene, glass, beads coated with different radical groups, methacrylate-styrene latex, traditional latex, polystyrene DVB. Possible fluorochromes include: Fluorescein isothiocyanate (FITC), Phycoerythrin (PE), Peridinin, Allochlorophyll (Per CP), Allophycocyanin, CY5, Texas Red, Propidium iodide, Ethidium bromide, and Acridine orange.

Antibodies which may be attached to beads or probes to detect antigens in body fluids include any monoclonal antibodies directed at infectious antigens such as, viruses, bacteria, parasites, fungi, and mycoplasma; autoantigens-(cell and cell components, such as nuclei, DNA, RNA nucleoli, membranes); cell products, such as collagen, reticulin, mucus, hormones, cytokines, neurotransmitters, coagulation factors, complement factors, mediators of inflammation (e.g. vasoconstrictive, chemotactic, enzymatic, phospholy), and enzymes; cell membrane antigens (erythrocytes-cross match, HLA-transplantation), and spermatozoa.

DNA or RNA may be attached to beads as molecular probes for the detection of infectious agents, particularly viruses (EBV, CMV, HIV, varicella-zoster, hepatitis, HPV, HCV, HBV, HTLV), oncogens and other disease related genes, in fluids by molecular hybridization.

Other examples of materials bound on control beads:
a) Antigens—RnP, Sm, SS-A, SS-B, Scl-70, dsDNA etc.
b) Antibodies—anti-p24, anti-HTLV, OKT3, etc.
c) Chemicals—IL-2, Toxins, drugs, etc.
d) Microorganisms—*E.coli*, HTLV, viruses, etc.
e) Cell components—IL-2R, Glycoproteins, etc.
f) DNA—double stranded complement strands, etc.
g) RNA—viral RNA, etc.
h) Others—cardiolipin, pollen, metals, recombinant products, etc.

EXAMPLE 16

Highly purified analytes are bound to respective μm latex beads having a diameter of greater than about 3.5 μm and stabilized for extended shelf life. Diluted control and patient's platelets are placed into selected test tubes containing a mixture of analyte coated beads and incubated. Next, an incubation with goat Ig-FITC or goat anti-human Ig-FITC is carried out.

Unbound conjugate is removed in the subsequent washing step. The fluorescence intensity is based on the avidity of the bead/analyte/conjugate binding. The samples are analyzed using flow cytometers having laser excitation wavelengths of 488 nm. Emission wavelengths are detected by photomultipliers which convert the fluorescent analog signals into digital signals two parameter histograms (size, Y-axis) versus fluorescent intensity (X-axis).

EXAMPLE 17

Allow test components and patient samples to warm to room temperature before use. Return promptly to refrigerator after use.
1. Properly label sufficient numbers of test tubes to identify positive patient control, negative control and patient samples.
2. Add 500 μL of bead solution into each of the labeled test tubes.
3. Prepare 1:100 dilutions of the positive patient control and negative control, and the patient samples, by adding 10 μL of each to 190 μL of sample diluent (in test tubes or microtiter plate provided).
4. Mix sample dilutions gently by withdrawing and expelling in a pipette tip 2 or 3 times (microtiter plate) or vortexing.
5. Transfer 15 μL of each diluted control or patient sample into corresponding test tube.
6. Gently vortex and incubate at room temperature (20–30° C.) for 15 minutes.
7. Add 1 mL of wash solution to each test tube.
8. Centrifuge for 10 minutes at 1500 g at 2–8° C.
9. Carefully decant supernatant and gently resuspend bead pellet by hand.
10. Add one drop (50 μL) of fluoresceinated conjugate to each tube.
11. Gently vortex and incubate for 15 minutes at room temperature in the dark.
12. Add 1 mL of wash solution to each tube.
13. Centrifuge for 10 minutes at 1500 g at 2–8° C.
14. Carefully decant supernatant and gently resuspend bead pellet by hand.
15. Add 1 mL of wash solution to each tube.
16. Analyze on flow cytometer.
NOTE: Analysis should be made within 2 hours of final staining.

EXAMPLE 18

Multiple Dye Bead Control and Assay
1. Determine the amount of latex bead suspension (e.g. # of drop w/mL carbonate buffer) needed to achieve an event count of 500–1000 beads/second on the flow cytometer.
2. Titer analytes (An) to appropriate μg/mL and use concentration deemed optimal for maximum mean channel and fluorescence.
3. Add a particular analyte to each respective tube (μg)

| Size bead, fluorescent dye | (Example of Drops/mL Buffer) | (Example of An/mL Buffer) |
| --- | --- | --- |
| 4 μm, PE | 3 | 30 |
| 5 μm, PE | 3 | 10 |
| 6 μm, PE | 6 | 15 |
| 7 μm, FITC | 6 | 15 |
| 10 μm, FITC | 10 | 10 |
| 12 μm, FITC | 10 | 10 |

4. Incubate bead/analyte mixture for 12–24 hours at 4–8° C.
5. Centrifuge solution at full speed in a refrigerated centrifuge for 10 minutes.
6. Decant supernatant and gently resuspend beads by hand.
7. Add 1 mL of control or patient platelets to appropriate tubes.
8. Gently vortex.
9. Repeat steps 5 and 6.
10. Add 1 mL of carbonate buffer per original milliliters of analyte/bead solution.
11. Add 100 μL of each analyte/bead or analyte/bead/platelet mixture to respective reaction tubes.
12. Add 50 μL of each serum to appropriately labeled tube.
13. Vortex gently and incubate for 15 minutes at room temperature.
14. Wash once with 1 mL Isotonic saline buffer.
15. Repeat steps 5 and 6.
16. Add 20 μL of goat Ig-FITC or goat anti-human Ig F(ab')$_2$FITC 1:20 (NOTE: dilution may slightly vary from lot to lot, titer all new lots).
17. Gently vortex and incubate 15 minutes at room temperature.
18. Repeat steps 5 and 6.
19. Add 1.0 mL of Isotonic saline.
20. Read on flow cytometer.

FIGS. 25–30 are histograms or cytograms of the bead or beads used with Type O platelets, platelets from a negative patient and a positive patient. When interpreting these cytograms, review the Type O map (FIGS. 22 and 31) for positioning of the beads relative to the cellular populations. The immunoglobulin (Ig) coating for IgG, M, and A is one polyvalent coated bead of 6 μm (as illustrated in the Forward Scatter versus Side Scatter cytograms). A negative, non-coated bead of the same 6 μm size is also added as the negative control indicator. This system works in the IgG, A, and M systems separately (see FIGS. 26, 30). The negative bead has been eliminated from the IgM tube in order to demonstrate that intensity remains constant without any non-coated beads. Some doublets do occur as an artifact. These are attributed to the substrate and do not interfere with the main purpose of the reagent and assay.

EXAMPLE 19

Ig Positive Control

Direct Procedure:
1. Add 100 μL of Ig control material to each of three tubes labeled Control, IgG, M and A, respectively.
2. Add patient and control platelets to control, IgG, M and A tubes, respectively.
3. Add goat Ig-FITC to control tubes and goat anti-human Ig-FITC, at proper concentration, to IgG, M and A tubes, respectively.
4. Incubate for 15 minutes in the dark.
5. Wash once with Isotonic saline and add 1 mL to final volume.
6. Read on flow cytometer using Fwd Scatter versus FL1.
7. Set positive region based on Control tube for that patient.

EXAMPLE 20

Ig Positive Control

Indirect Procedure:
1. Incubate Type O platelets with 100 μL of control or patient serum in tubes labeled Control, IgG, M and A.
2. After 15 minutes, wash tubes with 1 mL of isotonic saline.
3. Decant and gently vortex.
4. Add 100 μL of Ig control bead material to each tube labeled Control, IgG, M and A, respectively.
5. Add goat Ig-FITC to control tubes and goat anti-human Ig-FITC, at proper concentrations, IgG, M and A tubes, respectively.
6. Incubate for 15 minutes in the dark.
7. Wash once with isotonic saline and add 1 mL to final volume.
8. Read on flow cytometer using FWD Scatter versus FL1.
9. Set positive bead control region based on Control tube for that patient.

EXAMPLE 21

Ig Coating Procedure
1. Label three test tubes IgG, M, and A.
2. Place 1 mL of Carbonate buffer into each tube.
3. Place previously calculated amount of beads into each appropriate tube. (e.g. 4μ into IgG, 5μ into IgM, and 6μ into IgA). (Note: One bead size may be used for all these immunoglobulins.)
4. Gently vortex solution.
5. Centrifuge at full speed in a cold centrifuge for 5 minutes.
6. Decant and gently resuspend bead pellet.
7. QS to 1 mL with carbonate buffer and vortex.
8. Add previously determined quantity of human Ig to each tube. (e.g. 10 μg of IgG to IgG beads, 10 μg of IgM to IgM beads, etc.).
9. Gently vortex solution and cover.
10. Incubate for 18–24 hours at 4–8 degrees C.
11. Gently invert 4 to 6 times to resuspend beads.
12. Centrifuge for 5 minutes, at full speed, in a refrigerated centrifuge.
13. Decant supernatant and gently resuspend.
14. QS to 1 mL with carbonate buffer.

The above procedure is for the production of 1 mL of bead reagent (Ig control material). Increased volumes may be made by multiplying the reagents by the factor of total volume needed.

EXAMPLE 22

Ig Positive Control Assay—Direct Assay
1. Add 100 μL of respective Ig control reagent from Example 23 to tubes labeled IgG, IgM and IgA, respectively.
2. Add patient and control platelets to Control, IgG, IgM and IgA tubes, respectively.
3. Add goat Ig-FITC to control tube and goat anti-human Ig-FITC, at proper concentration, IgG, IgM and IgA tubes, respectively.
4. Incubate for 15 minutes in the dark.
5. Wash once with saline and add 1 mL isotonic saline to final volume.
6. Read on flow cytometer using Fwd Scatter versus FL1.
7. Set positive fluorescence region based on Control tube for that patient.

EXAMPLE 23

Ig Positive Control Assay—Indirect Assay
1. Incubate Type 0 platelets with 100 μL of control or patient serum in 4 tubes labeled Control, IgG, IgM and IgA.
2. After 15 minutes, wash tubes by adding 1 mL of isotonic saline and centrifuge.
3. Decant and gently vortex.
4. Add 100 μL of Ig control reagent from Example 23 to each tube labeled IgG, IgM and IgA, respectively.
5. Add goat Ig-FITC to control tube(s) and goat anti-human Ig-FITC, at proper concentrations, to IgG, IgM and IgA tubes, respectively.
6. Incubate for 15 minutes in the dark.
7. Wash once with saline and add 1 mL to final volume.
8. Read on flow cytometer using Fwd Scatter versus FL1.
9. Set positive fluorescence region based on Control tube for that patient.

EXAMPLE 24

Ig Control Reagent
1. Label three test tubes IgG, IgM, and IgA.
2. Place 1 mL of Carbonate buffer into each tube.
3. Place previously calculated amount of a different size bead into each appropriate tube. (e.g. 4 μm into IgG, 5 μm into IgM, and 6 μm into IgA)
4. Gently vortex solution.
5. Centrifuge at full speed in a cold centrifuge for 5 minutes.
6. Decant supernatant and gently resuspend.
7. QS to 1 mL with carbonate buffer and vortex.
8. Add previously determined quantity of a respective human Ig to each tube. (e.g. 10 μg of IgG to the 4 μm beads, 10 μg of IgM to the 5 μm beads, etc.).
9. Gently vortex solution and cover.
10. Incubate for 18–24 hours at 4–8° C.
11. Gently invert 6 times to resuspend beads.
12. Centrifuge for 5 minutes, at full speed, in a refrigerated centrifuge.
13. Decant supernatant and gently resuspend.
14. QS to 1 mL with carbonate buffer.

The above procedure is for the production of about 1 mL of bead reagent. Increased volumes may be made by multiplying the reagents by the factor of total volume needed.

EXAMPLE 25

Platelet Ig Positive Control Assay

Direct Procedure:
1. Add 100 μL of each Ig control reagent from Example 24 to each tube labeled IgG, IgM and IgA, respectively.
2. Add control platelets to a tube labeled Control and add patient platelets to the IgG, IgM and IgA tubes, respectively.

3. Add goat Ig-FITC to control tube(s) and goat anti-human Ig-FITC, at proper concentration, to each of the IgG, IgM and IgA tubes, respectively.
4. Incubate for 15 minutes in the dark.
5. Wash once with saline and add 1 mL of saline to final volume.
6. Read on flow cytometer using Fwd Scatter versus FL1.
7. Set positive fluorescence region based on Control tube for that patient.

EXAMPLE 26

Platelet Ig Positive Control Assay
Indirect Procedure:
1. Incubate Type O platelets with 100 μL of control or patient serum in tubes labeled Control, IgG, IgM and IgA.
2. After 15 minutes, wash tubes with 1 mL of isotonic saline.
3. Decant and gently vortex.
4. Add 100 μL of Ig control reagent from Example 26 to each tube labeled IgG, IgM and IgA, respectively. Add 100 μL each at IgG, IgA, and IgM to control tube.
5. Add goat Ig-FITC or goat anti-human Ig-FITC, at proper concentrations, to the Control, IgG, IgM and IgA tubes, respectively.
6. Incubate for 15 minutes in the dark.
7. Wash once with isotonic saline and add 1 mL isotonic saline to final volume.
8. Read on flow cytometer using Fwd Scatter versus FL1.
9. Set positive fluorescence region based on Control tube for that patient.

EXAMPLE 27

Platelet Ig Positive Control Reagent
1. Label three test tubes IgG, IgM, and IgA, respectively.
2. Place 1 mL of Carbonate buffer into each tube.
3. Place previously calculated amount of different sized μm beads into each appropriate tube. (e.g. 4 μm into IgG, 5 μm into IgM, and 6 μm into IgA)
4. Gently vortex solution.
5. Centrifuge at full speed in a cold centrifuge for 5 minutes.
6. Decant supernatant and gently resuspend.
7. QS to 1 mL with carbonate buffer and vortex.
8. Add previously determined quantity of respective human Ig to each tube. (e.g. 10 μg of IgG to the 4 μm beads, 10 μg of IgM to the 5 μm beads, etc.).
9. Gently vortex solution and cover.
10. Incubate for 18–20 hours at 4–8° C.
11. Gently invert 6 times to resuspend beads.
12. Centrifuge for 5 minutes, at full speed, in a refrigerated centrifuge.
13. Decant supernatant and gently resuspend.
14. QS to 1 mL with carbonate buffer.

The above procedure is for the production of 1 mL of each Ig bead reagent. Increased volumes may be made by multiplying the quantities by the factor of total volume needed.

EXAMPLE 28

Ig Positive Control Assay
Direct Procedure:
1. Add 100 μL of each of the Ig control coated beads of Example 26 to a respective tube labeled IgG, IgM and IgA.
2. Add goat Ig-FITC to Control tube(s) and goat anti-human Ig-FITC, at proper concentration, to each IgG, IgM and IgA tube, respectively.
3. Incubate for 15 minutes in the dark.
4. Wash once with isotonic saline and add 1 mL to final volume.
5. Read on flow cytometer using Fwd Scatter versus FL1.
6. Set positive fluorescence region based on Control tube for that patient.

EXAMPLE 29

Ig Positive Control
Indirect Procedure:
1. Add 100 μL of control or patient serum in respective tubes labeled Control, IgG, IgM and IgA.
2. Add 100 μL of respective Ig control coated beads of Example 29 to each of the tubes labeled IgG, IgM and IgA, respectively.
3. Add goat Ig-FITC to control tube(s) and goat anti-human Ig-FITC, at proper concentrations, to each IgG, IgM and IgA tubes, respectively.
4. Incubate for 15 minutes in the dark.
5. Wash once with isotonic saline and add 1 mL to final volume.
6. Read on flow cytometer using Forward Scatter versus FL1.
7. Set positive region based on Control tube for that patient.

EXAMPLE 30

Ig Control Coated Beads
1. Label three test tubes IgG, IgM, and IgA.
2. Place 1 mL of Carbonate buffer into each tube.
3. Place previously calculated amount of selected μm beads into each appropriate tube. (e.g. 8 μm into IgG, 10 μm into IgM, and 12 μm into IgA)
4. Gently vortex solution.
5. Centrifuge at full speed in a cold centrifuge for 5 minutes.
6. Decant supernatant and gently resuspend.
7. QS to 1 mL with carbonate buffer and vortex.
8. Add previously determined quantity of respective human Ig to each tube. (e.g. 10 μg of IgG to the 8 μm beads, 10 μg of IgM to the 10 μm beads, etc.).
9. Gently vortex solution and cover.
10. Incubate for 18–24 hours at 4–8° C.
11. Gently invert 6 times to resuspend beads.
12. Centrifuge for 5 minutes, at full speed, in a refrigerated centrifuge.
13. Decant supernatant and gently resuspend.
14. QS to 1 mL with carbonate buffer.

The above procedure is for the production of 1 mL of each Ig control coated bead reagent. Increased volumes may be made by multiplying the quantities by the factor of total volume needed.

EXAMPLE 31

Analyte Control Material
1. Label each test tube with a separate analyte to be tested.
2. Place 1 mL of Carbonate buffer into each tube.
3. Place previously calculated amount of a different sized, cibhygated, or shaped bead into each appropriate tube. (e.g. 4 μm into IgG, 5 μm into IgM, and 6 μm into IgA)
4. Gently vortex solution.
5. Centrifuge at full speed in a cold centrifuge for 5 minutes.
6. Decant supernatant and gently resuspend.
7. QS to 1 mL with carbonate buffer and vortex.
8. Add previously determined quantity of human Ig to each analyte in each tube. (e.g. 10 μg of IgG to the 4 μm beads, 10 μg of IgM to the 5 μm beads, etc.).
9. Gently vortex solution and cover.
10. Incubate for 18–24 hours at 4–8° C.
11. Gently invert 6 times to resuspend beads.
12. Centrifuge for 5 minutes, at full speed, in a refrigerated centrifuge.

13. Decant supernatant and gently resuspend.
14. QS to 1 mL with carbonate buffer.

The above procedure is for the production of 1 mL of analyte control material. Increased volumes may be made by multiplying the reagents by the factor of total volume needed.

EXAMPLE 32

Figure 32:
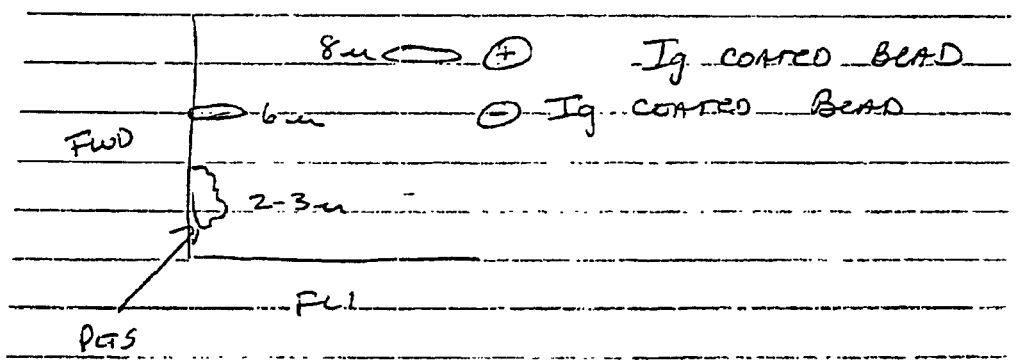
Figure 31C:
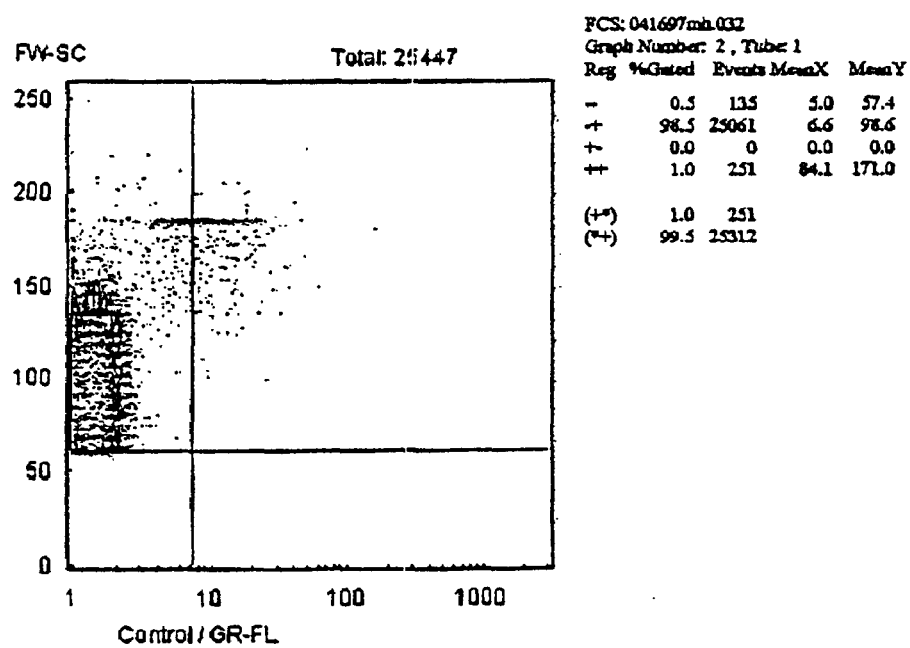

Platelet Evaluation Positive Control System (FIG. 32)
1. Coating of control beads (reagents) is the same as for the other kit(s) but no 0.5% albumin wash.
2. Use three different bead sizes for three different human Ig's or use one bead size for each of the three human Igs.
3. Also, can use different sized beads for the coated and uncoated (+ and −) beads.
4. Use beads in screening for IgG, IgA, and IgM label with specific goat anti-human IgG, IgA and IgM FITC conjugated antibody.

EXAMPLE 33

Antibody Control Material

New antibodies are produced (for example, against anti-CD34 antigen for stem cell transplantation monitoring) which the investigator has no way of testing the antibody for specificity, sensitivity, or purity to the specific epitope. Because the CD34 antigen only occurs in less than 2% of the normal bone marrow population, this evaluation would be very difficult to perform.

The invention would coat one size bead with a recombinant CD34 antigen (recombinator purified) as in the procedure seen in Example 16 and 17.
1. Label several tubes with the quantities of 1, 5, 10, 15 and 20 uL for quantity of CD34 antibody to be added.
2. Add 100 uL of CD34 antigen coated beads to each of the above tubes.
3. Add 1, 5, 10, 15, and 20 uL of anti-CD34 Antigen antibody to each of the appropriately labeled antibody tubes.
4. Gently vortex and incubate for 15 minutes at room temperature.
5. Add 1 mL of phosphate buffered saline (PBS) and centrifuge.
6. Decant and gently vortex.
7. Unless previously conjugated, add conjugated fluorescenated goat anti-species antibody to each of the antibody labeled tubes.
8. Gently vortex and incubate for 15 minutes in the dark, at room temperature.
9. Repeat steps 5 and 6.
10. Add 1 mL of PBS, vortex.
11. Read on flow cytometer using forward scatter versus FL1 channel or Forward versus side scatter and gate around the beads. Read gated material and transfer information to a single parameter fluorescent histogram.
12. Use a negative, non-anti-CD34 antibody as a control for adjustment of any flourescent mean channel settings.

EXAMPLE 34

Analyte/Antibody Reactivity Confirmation Usage

With the efficiency of the current invention, new analytes to be tested or used in clinical instrumentation maybe screened for reactivity prior to implementation on the system. For example, clinical chemistry analyzers typically utilize antibody/antigen reactions for the detection of lipoproteins and electrolytes. Manufacturing these products poses great problems for the specificity and sensitivity of the specific component antibodies.

As with Example 33 above and with the availability of fluorescenated antibodies, lipoproteins and electrolytes can be coated onto different size beads. Antibodies to these analytes used in the chemistry system can be incubated with these beads. Assuming that all the antibodies are from one species, an anti-species specific fluorescenated antibody can be added to detect formation of the analyte/antibody complex.

From this, if positive fluorescence in proven for a specific size bead, with a specific analyte/antibody complex, the manufacturer of that combination would be secure in their quality assurance that the combination will initially work in the chemistry analyzer.

EXAMPLE 35

Recombinant Protein Detection

Positive antibody controls have significant importance in the detection of recombinant proteins (e.g. viral particles, bacteria, proteins, etc.) which may of may not have substrate specific antibodies. Furthermore, a new recombinant protein maybe invented, however, the investigator may not be sure of which general antibodies will bind the recombinant sequences and to what degree. Protein antigenicity is important in many different assays. Positive bead controls, like the anti-Platelet Immunoglobulin Control, provide confirmation of antigenetic prior to use in assays such as ouchterlony, ELISA, and Western Blot, thus saving time and reagents.

To determine if a specific repertoire of antibodies will detect a specific recombinant product (antigen), coated single or multisized beads with the protein.
1. Label appropriate tubes with the names of the antigens.
2. Add 100 uL of recombinant protein coated bead to each tube.
3. Add vendor specific amount of positive antibody to each of the properly labeled tubes.
4. Incubate for 15 minutes at room temperature.
5. Add 1 mL of PBS, vortex and centrifuge for 5 minutes at 800 g (optional).
6. Decant and vortex (do not complete if step 5 not done).
7. Add vendor specific amount of anti-species fluorescenated antibody and incubate for 15 minutes in the dark at room temperature. (If primary positive control antibody was conjugated with a fluorescent dye, go to step 9.)
8. Repeat steps 5 and 6 (optional, do only if step 5 was completed).
9. Add 1 mL of PBS and read on flow cytometer.

Interpretation

Each antibody, if reactive against the specific protein, should fluoresce and to varied degrees of intensity; those which do not react positively will be eliminated from the protocol of usage because of non-identity.

EXAMPLE 36

Bacterial Antigen Species Positive Control—Multicolor Approach

Many lyophilyzed bacterial cultures are available to detect multiple species strains. These assays are especially useful in the therapeutic regime physicians require on patients with bacteremia.

Bacterial positive antibody controls coated with species specific bacterial antigens may provide a useful tool to determine specificity of an infection by utilizing the invention with multi-colored size specific beads. Patient antibodies against these antigens (bacterial positive control products) will bind to the beads.

In combination with multiple fluorochromes for anti-human IgG and anti-human IgM, the infectious stage of the patient can also be determined, IgG positive being convalescent, IgM positive being acute.

Similarly to the invention, this plurality of bacteria coated beads versus human immunoglobulin coated beads, provides a know positive control substrate for any assay quantifying or qualifying immunoglobulin specific reactions.

Interpretation

Multi-color analysis may confirm whether the initial ELISA substrate accurately detected the presence of an anti-IgG or anti-IgM antibody.

With a known, multisized bead control containing different strains, together with fluorescently unique detector antibodies, the confirmatory positive control system would enhance the standard detection assays and/or confirm that reagents are working properly.

EXAMPLE 37

Quantitative Negative Extraction Control

Previous work with beads and quantitation have lead to the development of known quantities of fluorescent molecules attached to specific beads as standards and then analyzed on the flow cytometer (Schwartz). Quantitation of material on cell surfaces was then indirectly quantitated in mean immunofluorescent (MIF) units based on the mean channel fluorescence of the cells in relation to the MIF curve created by the fluorescent bead standards.

Within the embodiment of this invention, we have found a direct method for the quantitation for antibody binding sites base on Control positive control beads.

Each cluster designation (CD) antigen is related to a specific site on one or more cell types. These antigen densities are important for the production of antibodies against these sites and the outcome of the fluorescent intensity. Logistically, these antibodies, based on the manufacturers recommended quantity/cell count, should saturate all receptors within that mixture based on "average" quantities.

These cellular antigen concentrations are generally known, however, antibody manufacturers titer on specific cell lines to achieve optimal packaging concentrations. Within the embodiment of the invention, these positive bead controls can be coated with known quantities of antigen similar to that of the cellular densities. Antibodies against these antigens can be incubated with the bead and absorbed. These beads can then be centrifuged and the supernatant saved. By adding the supernatant to another series of antigen coated bead(s), centrifuging, saving the supernatant, and then applying a fluorescent anti-species detector secondary antibody, the invention would detect if there was antibody excess to cover the epitopes known to exist at maximum concentration. See example below.

EXAMPLE 38

Interleukin Density Detection Control

Coating a plurality of latex particles with unique antigens for Interleukin (IL) receptor detection based on known concentrations of IL receptor densities on specific cellular lineages. These beads are of known, positive concentrations for ILr-2 and ILr-4.

Purpose: To determine if an anti-ILr-2 and anti-ILr-4 antibody hybridoma can saturate the receptors of a normal lymphocyte population by flow cytometry.

1. Determine the appropriate amount of ILr-2 and ILr-4 antigen to use given a specific amount of surface area of a 10 micron bead suspension in carbonate buffer, pH 4 to 10.
2. Add this amount to each of two separate bead suspensions, one for ILr-2 and ILr-4, respectively.
3. Incubate the bead/ILr solution for approximately 12–24 hours at 4 degrees centigrade.
4. Centrifuge the bead suspension at 800 g for 10 minutes.
5. Decant the supernatant and gently resuspend the bead pellet.
6. Resuspend the beads in enough carbonate buffer to a concentration of 10 million beads per milliliter.
7. Add 100 uL of each bead suspension to separate tubes.
8. Add vendor specific amounts of anti-ILr-2 and ILr-4 antibody to ILr-2 and ILr-4 tubes, respectively.
9. Incubate tubes for 15 minutes at room temperature.
10. Centrifuge tubes at 800 g for 5–10 minutes.
11. Carefully aspirate supernatant from each tube and transfer to separate tubes. Save supernatant!
12. To confirm initial antigen/antibody binding, carefully vortex bead pellets in each tube.
13. Add vendor specific amounts of a species specific fluorescenated secondary antibody to the bead suspension.
14. Gently vortex and incubate for 15 minutes, room temperature, in the dark.
15. Read on flow cytometer.
16. If positivity is over 90% then reincubate supernatant with new beads and repeat steps 7 through 15 until positive drop-off off binding detected.

Interpretation: This procedure is utilized for the determination of antibody saturation to a known receptor concentration. As a control bead system, this procedures may be used to determine affinity of antigen/antibody systems.

Thus it will be appreciated that, as a result of the present invention, a highly effective improved assay, reagent, control kit and system are provided by which the principal objective, among others, is completely fulfilled. It is contemplated, and will be apparent to those skilled in the art from the preceding description and accompanying drawings, that modifications and/or changes may be made in the illustrated embodiments without departing from the present invention. Accordingly, it is expressly intended that the foregoing description and accompanying drawings are illustrative of preferred embodiments only, not limiting, and that the true spirit and scope of the present invention be determined by reference to the appended claims.

What is claimed is:

1. A process for producing anti-platelet Ig control coated beads for flow cytometric assays, comprising the steps of:

labeling three test-tubes IgG, IgM and IgA;

placing a carbonate buffer into each of the three test-tubes;

placing an amount of micron beads into each of the three test-tubes, the micron beads in each test-tube having a predetermined size;

gently vortexing the resulting solution;

centrifuging the solution to substantially separate the beads from the buffer solution;

removing the supernatant buffer solution from the beads;

vortexing the beads to create a uniform suspension;

adding an amount of carbonate buffer to the beads sufficient to achieve resuspension of the beads;

adding one or immunoglobulins IgG, IgM and IgA to each of the three test-tubes labeled IgG, IgM and IgA respectively;

vortexing the resulting solution;

incubating the solution until attachment of the immunoglobulin to the beads has occurred;

resuspending the buffer/bead mixture;

centrifuging the buffer/bead mixture to separate out unattached immunoglobulin;

decanting supernatant immunoglobulin-coated beads and gently resuspending; and adding an amount of carbonate butter to stabilize the coated beads.

2. A process as claimed in claim 1 wherein three different immunoglobulins are added to each test-tube.

3. A process as claimed in claim 2 wherein the three immunoglobulins are attached to beads of one size.

4. A process as claimed in claim 2 wherein each of the immunoglobulins is attached to beads of different sizes.

5. A process as claimed in claim 1 wherein incubation takes place for 18 to 24 hours at 4–8° C.

6. A process as claimed in claim 1 further comprising the step of gently inverting the buffer/bead mixture six times, to re-suspend the beads after incubation.

7. A process as claimed in claim 1 wherein 1 ml of carbonate buffer is added to the test tube in each of the steps where carbonate buffer is added.

8. A process as claimed in claim 1 wherein two different immunoglobulins are added to each test tube.

9. A process as claimed in claim 1 wherein a subclass of IgG, IgM and IgA is added.

10. A process as claimed in claim 3 wherein beads of one size are impregnated with fluorescent dyes.

11. A process as claimed in claim 1 wherein serum protein for blocking non-specific binding is added to the buffer solution.

12. A process as claimed in claim 1 wherein the immunoglobulins IgG, IgM and IgA are human immunoglobulins XgG, IgM and IgA.

* * * * *